(12) United States Patent
Slifka et al.

(10) Patent No.: US 8,716,000 B2
(45) Date of Patent: *May 6, 2014

(54) INACTIVATING PATHOGENS WITH OXIDIZING AGENTS FOR VACCINE PRODUCTION

(75) Inventors: Mark K. Slifka, Banks, OR (US); Shirley Villadiego, Miami, FL (US); Erika Hammarlund, Hillsboro, OR (US); Paul Yoshihara, Portland, OR (US)

(73) Assignee: Oregon Health and Science University, Portland, OR (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/405,082

(22) Filed: Feb. 24, 2012

(65) Prior Publication Data

US 2013/0004525 A1  Jan. 3, 2013

Related U.S. Application Data

(63) Continuation of application No. 11/500,763, filed on Aug. 7, 2006, now Pat. No. 8,124,397.

(60) Provisional application No. 60/706,555, filed on Aug. 8, 2005.

(51) Int. Cl.
*C12N 7/06* (2006.01)
*C12N 7/00* (2006.01)
*C12N 7/01* (2006.01)
*C12N 7/04* (2006.01)
*A61K 39/00* (2006.01)
*A61K 39/38* (2006.01)

(52) U.S. Cl.
USPC ...... 435/238; 435/235.1; 435/236; 424/184.1

(58) Field of Classification Search
CPC .............. A61K 33/40; A61K 2300/00; A61K 41/0009; A61K 39/00; A61K 41/0023; A61K 2039/525; A61K 2039/57; A61K 38/00; A61K 38/21; A61K 38/36; A61K 38/363; A61K 38/45; A61K 39/42; A61K 9/0043; A61K 2039/555; A61K 2039/55555; A61K 2039/5566; A61K 2039/60; A61K 2039/6068; A61K 31/05; A61K 31/075; A61K 31/145; A61K 38/1719; A61K 38/47; A61K 39/145; A61K 39/155; A61K 39/165; A61K 39/21; A61K 39/39; A61K 45/06; A61K 48/0075; A61K 48/0083; C12Q 1/6897; C12Q 1/68; C12N 15/8237; C12N 15/8234; C12N 15/8235; C12N 15/8247; C12N 15/8271; C12N 15/8238; C12N 2740/16122; C12N 2760/16122; C12N 9/0065; C12N 15/8239; C12N 2710/16222; C12N 2710/16711; C12N 2730/10122; C12N 2740/15022

USPC .............. 424/185.1, 184.1, 277.1; 435/320.1, 435/325, 235.1
See application file for complete search history.

(56) References Cited

U.S. PATENT DOCUMENTS

| | | |
|---|---|---|
| 3,932,943 A | 1/1976 | Briggs et al. |
| 4,134,214 A | 1/1979 | Graham et al. |
| 4,181,128 A | 1/1980 | Swartz |
| 4,235,871 A | 11/1980 | Papahadjopoulos et al. |
| 4,501,728 A | 2/1985 | Geho et al. |
| 4,622,222 A | 11/1986 | Horvath et al. |
| 4,710,378 A | 12/1987 | Ohtomo et al. |
| 4,837,028 A | 6/1989 | Allen |
| 4,902,505 A | 2/1990 | Pardridge et al. |
| 4,957,735 A | 9/1990 | Huang |
| 5,004,697 A | 4/1991 | Pardridge |
| 5,019,369 A | 5/1991 | Presant et al. |
| 5,055,303 A | 10/1991 | Riley, Jr. |
| 5,188,837 A | 2/1993 | Domb |
| 5,254,342 A | 10/1993 | Shen et al. |
| 5,268,164 A | 12/1993 | Kozarich et al. |
| 5,270,202 A | 12/1993 | Raychaudhuri |
| 5,271,961 A | 12/1993 | Mathiowitz et al. |
| 5,413,797 A | 5/1995 | Khan et al. |
| 5,506,206 A | 4/1996 | Kozarich et al. |
| 5,514,670 A | 5/1996 | Friedman et al. |
| 5,534,496 A | 7/1996 | Lee et al. |
| 5,580,557 A | 12/1996 | Kramer |

(Continued)

FOREIGN PATENT DOCUMENTS

| | | |
|---|---|---|
| GB | 933711 | 8/1963 |
| JP | 55118420 | 9/1980 |

(Continued)

OTHER PUBLICATIONS

Adams, "Lyophilization of Vaccines: Current Trends," *Methods in Molecular Medicine*, 2003, pp. 223-243, vol. 87.

(Continued)

*Primary Examiner* — Vanessa L Ford
*Assistant Examiner* — Lakia Tongue
(74) *Attorney, Agent, or Firm* — Barry L. Davison; Davis Wright Tremaine LLP

(57) ABSTRACT

The present disclosure provides methods for producing a vaccine composition containing a pathogen that is rendered noninfectious by exposure to hydrogen peroxide. The methods disclosed herein are suitable for the preparation of vaccines for a wide variety of pathogens, including viruses, bacteria and parasites. The disclosure also provides vaccine compositions (medicaments) containing a pathogen inactivated by exposure to hydrogen peroxide. Methods for eliciting an immune response in a subject by administering vaccine compositions containing a hydrogen peroxide inactivated pathogen are also provided.

13 Claims, 5 Drawing Sheets

(56) References Cited

U.S. PATENT DOCUMENTS

| | | | |
|---|---|---|---|
| 5,585,103 | A | 12/1996 | Raychaudhuri et al. |
| 5,662,907 | A | 9/1997 | Kubo et al. |
| 5,695,770 | A | 12/1997 | Raychaudhuri et al. |
| 5,709,860 | A | 1/1998 | Raychaudhuri et al. |
| 6,136,586 | A | 10/2000 | Budowsky |
| 6,399,076 | B2 | 6/2002 | Vose et al. |
| 6,436,402 | B1 | 8/2002 | Zhao et al. |
| 6,562,350 | B1 | 5/2003 | Wang et al. |
| 6,605,064 | B2 | 8/2003 | Hatch |
| 6,651,655 | B1 | 11/2003 | Licalsi et al. |
| 6,884,422 | B1 | 4/2005 | Liu et al. |
| 6,890,542 | B2 | 5/2005 | Mottram et al. |
| 7,098,309 | B2 | 8/2006 | Zhao et al. |
| 7,560,113 | B2 | 7/2009 | Christensen |
| 8,124,397 | B2 * | 2/2012 | Slifka et al. ............... 435/235.1 |

FOREIGN PATENT DOCUMENTS

| | | |
|---|---|---|
| WO | WO 99/13906 | 3/1999 |
| WO | WO 2004/002521 | 1/2004 |
| WO | WO 2005/001059 | 1/2005 |
| WO | WO 2005/007174 | 1/2005 |

OTHER PUBLICATIONS

Belding et al., "Peroxidase-Mediated Virucidal Systems," *Science*, Jan. 9, 1970, pp. 195-196, vol. 167, No. 915.

Bioreliance, Aseptic Filling and Lyophilization (2 pages), accessed on Jul. 14, 2008.

Deres et al., "In vivo priming of virus-specific cytotoxic T lymphocytes with synthetic lipopeptide vaccine," *Nature*, 1989, pp. 561-564, vol. 342.

Dodin, "Effect of a chemical system generative of hydroxyl free radicals on antigenicity. Application to the plague bacillus," *C. R. Hebd. Seances Acad. Sci.*, Mar. 2, 1964, pp. 2707-2710, vol. 258 (English translation of Abstract included).

Dunford, "Kinetics and Mechanisms of Mammalian Heme Peroxidase Reactions," *Progress in Reaction Kinetics and Mechanism*, 2005, pp. 245-265, vol. 30.

Dunford et al., "On the Mechanism of Chlorination by Chloroperoxidase," *Archives of Biochemistry and Biophysics*, 1987, pp. 292-302, vol. 252, No. 1.

Eaton, "Experimental Immunization of Mice with the Virus of Epidemic Influenza (Part I. Quantitative Studies on the Antigenicity of Active and Inactive Virus)," *The Journal of Immunology*, 1940, pp. 43-55, vol. 39.

EPA Guidance Manual: Alternative Disinfectants and Oxidants, "Peroxone (Ozone/Hydrogen Peroxide)," 21 pages, Apr. 1999.

"FDA Approves Certiva Vaccine for Diphtheria, Tetanus and Pertussis," Jul. 30, 1998, retrieved from http://www.pslgroup.com/dg/9139a.htm on Dec. 10, 2008.

Fults et al., "Sustained-Release of Urease from a Poloxamer Gel Matrix," Journal of Parenteral Science and Technology, Mar.-Apr. 1990, pp. 58-65, vol. 44, No. 2.

Griffiths et al., "Assuring the Quality and Safety of Vaccines: Regulatory Expectations for Licensing and Batch Release," *Methods in Molecular Medicine*, 2003, pp. 353-376, vol. 87.

Hammarlund et al., "Duration or antiviral immunity after smallpox vaccination," *Nature Medicine*, 2003, pp. 1131-1137, vol. 9, No. 9.

Hammarlund et al., "Multiple diagnostic techniques identify previously vaccinated individuals with protective immunity against monkeypox," *Nature Medicine*, 2005, pp. 1005-1011, vol. 11, No. 9.

Handrick et al., "The virucidal effect of hydrogen peroxide," *Z Gesamte Hyg.*, 1969, pp. 612-616, vol. 15, No. 8 (English translation of Summary on p. 615).

Hansen et al., "Curvularia Haloperoxidase: Antimicrobial Activity and Potential Application as a Surface Disinfectant," *Applied and Environmental Microbiology*, 2003, pp. 4611-4617, vol. 69, No. 8.

Hunter et al., "The adjuvant activity of nonionic block polymer surfactants. I. The role of hydrophile-lipophile balance," *J. Immun.*, 1981, pp. 1244-1250, vol. 127, No. 3.

Hunter et al., "The adjuvant activity of nonionic block polymer surfactants. II. Antibody formation and inflammation related to the structure of triblock and octablock copolymers," *J. Immun.*, 1984, pp. 3167-3175, vol. 133, No. 6.

Ibsen, "The effect of formaldehyde, hydrogen perioxide and genetic detoxification of pertussis toxin on epitope recognition by murine monoclonal antibodies," *Vaccine*, 1996, pp. 359-368, vol. 14, No. 5.

Ijntema et al., "Hydroxyapatite microcarriers for biocontrolled release of protein drugs," *Int. J. Pharm.*, 1994, pp. 215-224, vol. 112.

Johnston et al., "Sustained delivery of interleukin-2 from a poloxamer 407 gel matrix following intraperitoneal injection in mice," *Pharm. Res.*, 1992, pp. 425-434, vol. 9, No. 3.

Langer, "Polymer-Controlled Drug Delivery Systems," Ace. Chem. Res., 1993, pp. 537-542, vol. 26.

Mentel et al., "Investigations on Rhinovirus Inactivation by Hydrogen Peroxide," *Acta. Viral.*, 1973, pp. 351-354, vol. 17.

Neighbor et al., "The Effect of Microaerosolized Hydrogen Peroxide on Bacterial and Viral Poultry Pathogens," *Poultry Science*, 1994, pp. 1511-1516, vol. 73.

Rensselaer Polytechnic Institute, "Principles of Lyophilization Equipment," retrieved Apr. 14, 2004, from http:www.rpi.edu/depUchem-eng/Biotech-Environ/LYO/section3.html) (2 pages).

Roberts et al., "Inactivation of human immunodeficiency virus type 1, hepatitis A virus, respiratory syncylial virus, vaccinia virus, herpes simplex virus type 1, and poliovirus type 2 by hydrogen peroxide gas plasma sterilization," *American Journal of Infection Control*, Apr. 1998, pp. 94-101, vol. 26, No. 2.

Sattar et al., "Germicide Inactivation of Hepatitis B and C Viruses," *Public Health Agency of Canada*, 2001, 10 pages, vol. 27S3.

Terres, "Part 1: Effect of Hydrogen Peroxide Oxidation on the Antigenicity of Ovalbumin, Bovine Serum Albumin, and Rabbit Gamma Globulin. Part II: Cortical Discontinuity and Propagation of Spreading Depression," thesis presented "In Partial Fulfillment of the Requirements for the Degree of Doctor of Philosophy," *California Institute of Technology*, Pasadena, California, 1956.

Tleugabulova et al., "Aggregation of recombinant hepatitis B surface antigen induced in vitro by oxidative stress," *Journal of Chromatography B*, 1999, pp. 153-166, vol. 736.

Winter et al., "Bleach Activates a Redox-Regulated Chaperone by Oxidative Protein Unfolding," *Cell*, 2008, pp. 691-701, vol. 135.

Zhao et al., "Maturation of Recombinant Hepatitis B Virus Surface Antigen Particles," *Human Vaccines*, 2006, pp. 174-180, vol. 2.

* cited by examiner

INACTIVATING PATHOGENS WITH OXIDIZING AGENTS FOR VACCINE PRODUCTION

CROSS-REFERENCE(S) TO RELATED APPLICATION(S)

This application is a continuation of U.S. patent application Ser. No. 11/500,763, filed 7 Aug. 2006 (now U.S. Pat. No. 8,124,397, issued on 28 Feb. 2012), and further claims the benefit of priority to U.S. Provisional Application Ser. No. 60/706,555, filed Aug. 8, 2005, both of which are incorporated herein by reference in their entirety for all purposes.

FIELD

The present disclosure relates to the field of vaccines. More specifically, the disclosure relates to methods of preparing vaccines by inactivating the pathogen with hydrogen peroxide.

BACKGROUND

Current methods used to inactivate living pathogens in vaccine production involve the use of chemical agents such as formaldehyde or betapropiolactone to chemically modify the genetic material of the pathogen. However, there is substantial evidence that both of these agents are human and animal carcinogens. For example, studies in rats exposed to formaldehyde by inhalation have shown that formaldehyde induces squamous-cell carcinoma of the nasal cavity. Additionally, formaldehyde has been shown to be genotoxic in vitro and in vivo. Both genotoxicity and cytotoxicity play an important role in the carcinogenicity of formaldehyde.

Although the concentration of formaldehyde in vaccines is typically low (below 0.02%), this represents up to 50-100 micrograms of formaldehyde per injected dose in many vaccines (for example, Anthrax vaccine produced by Bioport Corp. contains 100 microgram/ml formaldehyde as a preservative) and poses a potential hazard due to the number of vaccinations a person receives over the course of a lifetime. Particularly dangerous is the amount of formaldehyde that is injected into infants and small children during the course of multiple routine childhood vaccinations. While the amount of formaldehyde in each vaccine dose is low, the combined amount can become substantial.

Similarly, betapropiolactone, which is used in the inactivation of rabies virus, can produce an immune complex-reaction when combined with other components of the rabies vaccine. Additionally, it has been shown to produce squamous cell carcinomas, lymphomas and hepatomas in mice.

Thus, there is a need to develop a low cost, nontoxic alternative to formaldehyde and betapropiolactone for the inactivation of live pathogens, such as viruses, bacteria and parasites. The methods disclosed herein address this need, and provide substantial benefits not previously described in the art.

SUMMARY

The present disclosure provides methods for producing an immunogenic composition such as a vaccine (for example, methods for preparing a medicament) containing an inactivated pathogen, such as an inactivated whole pathogen. The methods involve contacting the pathogen with a solution including an effective amount of an oxidizing agent, such as hydrogen hydrogen peroxide, for a period sufficient to render the pathogen noninfectious. The disclosed methods result in a preservative-free vaccine composition that is substantially free of hydrogen peroxide, without the necessity of any intervening purification step.

The methods disclosed herein are suitable for the preparation of immunogenic compositions (for example, vaccines) for a wide variety of pathogens, including viruses, bacteria and parasites (e.g., intracellular parasites).

Also disclosed are immunogenic compositions, such as vaccines containing an inactivated pathogen. For example, the composition (or medicament) can be a lyophilized immunogenic composition (for example, vaccine preparation) containing a pathogen that retains one or more predominant antigenic epitopes of the biologically active pathogen from which it was prepared. The lyophilized composition is preservative-free and devoid of any inactivating agent. The composition can also be a liquid prepared by reconstituting the lyophilized composition in a pharmaceutically acceptable diluent. Optionally, the composition can include a suitable adjuvant that increases the antigenic efficacy of the antigen.

Methods for eliciting an immune response in a subject by administering the compositions containing inactivated pathogen are also described.

The foregoing and other objects, features, and advantages of the invention will become more apparent upon review of the following detailed description and accompanying figures.

BRIEF DESCRIPTION OF THE DRAWINGS

FIG. 5A is a bar graph illustrating virus titer (pfu/ml) of several different viral pathogens inactivated (+) with 3% $H_2O_2$ or untreated (−). From left to right: lymphocytic choriomeningitis virus (LCMV); vaccinia virus (VV); monkeypox virus (MPV); yellow fever virus (YFV); and West Nile virus (WNV). FIG. 5B is a bar graph illustrating inactivation of LCMV at a wide range of $H_2O_2$ concentrations. Virus titer is indicated in pfu/ml.

DETAILED DESCRIPTION

Introduction

Figure 1:
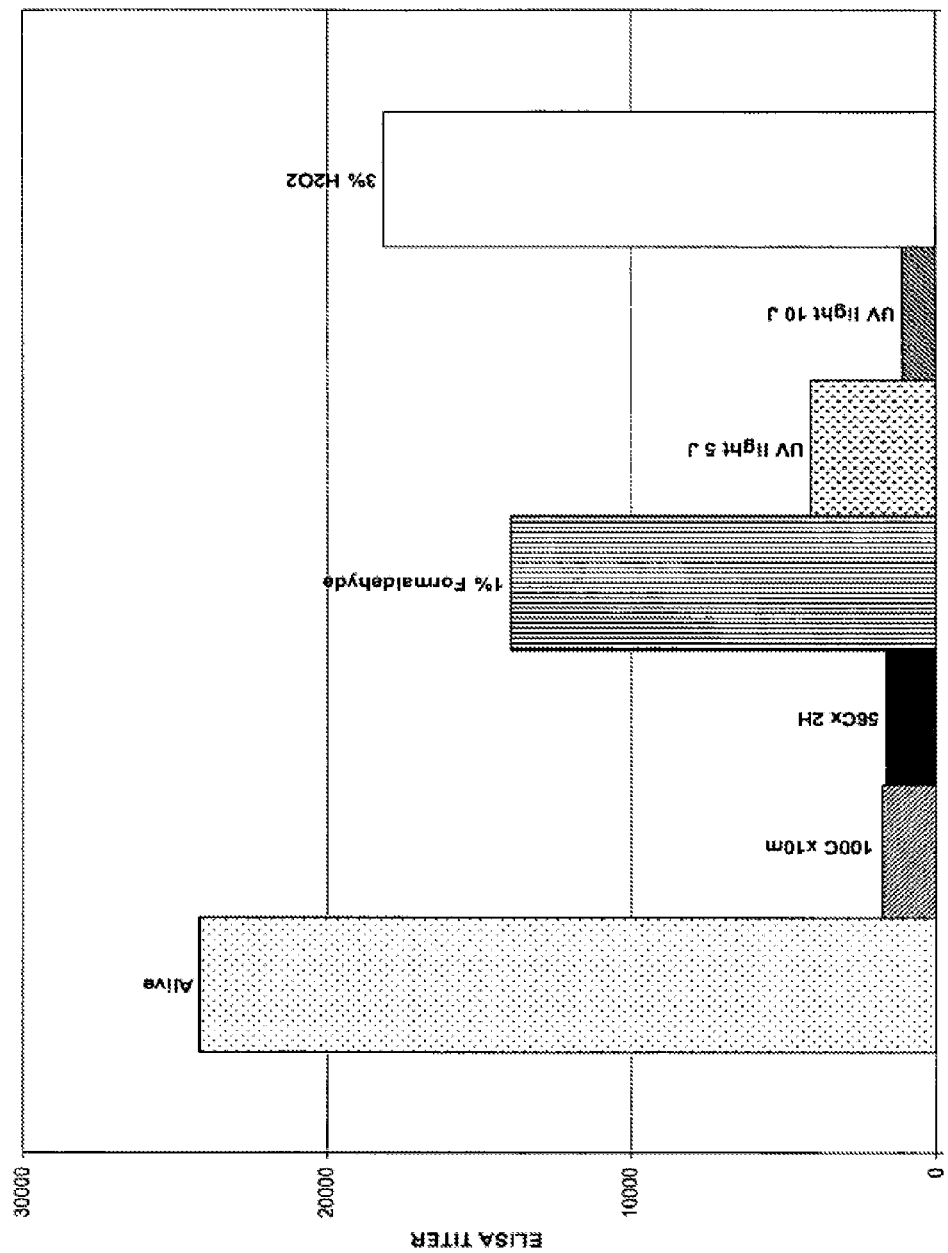
FIG. 1 is a bar graph illustrating the results of an ELISA that measures the antigenicity of different preparations of inactivated vaccinia virus (VV) antigen compared to untreated live virus. In each cases, equal quantities of virus antigen were used to coat the ELISA plate and human serum from a vaccinia-immune volunteer (Dryvax; live smallpox vaccine) was used to determine how well the inactivated virus antigen could be recognized by VV-immune serum. The results of different inactivation methods are shown from left to right: live vaccinia virus-no inactivation treatment; 100° C. for 10 minutes; 56° C. for 2 hours; 1% formaldehyde; UV light-5 Joules; UV light-10 Joules; 3% $H_2O_2$. Titer value is indicated on the Y axis.

The present disclosure provides methods for producing immunogenic compositions, such as vaccines, by exposing pathogens to an oxidizing agent, such as hydrogen peroxide. Hydrogen peroxide possesses broad-spectrum antimicrobial activity, and effectively inactivates a wide range of pathogens, including viruses, bacteria, and parasites. Non-replicating vaccines have typically been prepared by treating live pathogens with ultraviolet light (UV inactivation), by heat (heat inactivation) or by chemical inactivation with toxic and carcinogenic agents, such as formaldehyde and betapropiolactone. Although hydrogen peroxide has been used in producing purified pertussis toxin protein for vaccine use (see, e.g., Ibsen et al., Vaccine 14:359-368, 1996), the utility of hydrogen peroxide in the production of vaccine compositions from live pathogens has previously gone unrecognized.

Inactivation with an oxidizing agent, such as hydrogen peroxide, provides several significant benefits as compared to UV inactivation, heat inactivation or inactivation with formaldehyde or betapropiolactone. Hydrogen peroxide is significantly better than any of the other methods at maintaining immunogenic epitopes. Thus, hydrogen peroxide inactivation produces a highly effective immunogenic composition, such as a vaccine, that can be used to produce an immune response that is far more likely to be protective against subsequent infection by the live pathogen than are vaccines produced using methods that denature immunologically important epitopes.

Unlike other chemical inactivating agents, such as formaldehyde or betapropiolactone, hydrogen peroxide can be substantially or completely removed from the vaccine composition by lyophilization. Thus, a solution containing a pathogen and hydrogen peroxide can be dispensed into sterile vials and lyophilized. During the lyophilization process, hydrogen peroxide is removed in vapor form, leaving behind a stable and sterile vaccine composition, which can easily be stored until it is needed. Prior to use, the vaccine can be reconstituted using a pharmaceutically acceptable diluent to facilitate delivery by conventional administration means. This enables the production of a sterile vaccine composition that does not contain harmful amounts of toxic and carcinogenic compounds, thereby increasing the safety of the vaccine.

Additionally, following inactivation with hydrogen peroxide, there is no need to add a preservative (such as thimerosal) to the resulting vaccine composition. The sterile composition can be maintained for long periods of time in the lyophilized state, making addition of potentially toxic preservatives unnecessary. Thus, in certain embodiments, the compositions are substantially or completely free of preservatives. Preservatives can of course optionally be provided in the composition.

Thus, one aspect of the disclosure relates to a method for producing an immunogenic composition, such as a vaccine (for example, methods for preparing a medicament) that includes an inactivated pathogen. This method results in the production of a composition that contains an immunologically active noninfectious pathogen. That is, the inactivated pathogen retains the predominant immunological epitopes of the infectious pathogen from which it is produced. Typically, the inactivated pathogen retains one, or more than one, immunologically dominant epitopes that elicit a protective immune response against the pathogen. This method is suitable for producing an immunogenic composition (for example, a vaccine) containing inactivated pathogens, including viruses, bacteria, fungi and parasites, such as intracellular parasites (for example, protozoan parasites). Optionally, the composition contains more than one species or strain of pathogen, for example, the composition is a combination vaccine. In one example, the composition can include a plurality of viruses, e.g., mumps virus, measles virus and rubella virus. Similarly, the composition can include a plurality of bacteria, e.g., *Corynebacterium diptheriae*, *Bordatella pertussis* and *Clostridium tetani*, the causative agents of diphtheria, whooping cough and tetanus, respectively. The composition can also include a plurality of pathogens selected from different classifications (families) of organisms.

The method involves contacting the pathogen with a solution containing an effective amount of an oxidizing agent, such as hydrogen peroxide ($H_2O_2$) for a period sufficient to render the pathogen noninfectious. Optionally, the pathogen is purified or isolated prior to contacting with hydrogen peroxide. Typically, the solution includes at least about 0.1% hydrogen peroxide (wt/vol), and may contain up to about 30% hydrogen peroxide. For example, the solution can include about 0.5% hydrogen peroxide, about 1% hydrogen peroxide, about 1.5% hydrogen peroxide, or about 2% hydrogen peroxide. In certain embodiments, the solution contains about 3% hydrogen peroxide. For example, 3% hydrogen peroxide solutions are readily available from commercial suppliers, as are 30% solutions. Thus, 3% is a convenient concentration. However, for example, any concentration between about 0.1% and 30% can be used. The length of time sufficient to completely inactivate a pathogen can vary between several seconds (e.g., ten seconds) and about two hours. For example, the pathogen can be contacted with the hydrogen peroxide solution for about five minutes or about 30 minutes or about 1 hour. Generally, the length of time sufficient to inactivate the pathogen is inversely related to the concentration of hydrogen peroxide in the inactivating solution, and can be determined empirically by one of ordinary skill in the art. The inactivation can be carried out at any temperature between freezing and the temperature at which immunologically relevant epitopes are denatured. Most commonly, the inactivation process is carried out at or above 4° C. and below about 42° C. For example, it is often convenient to perform the inactivation at room temperature or about 25° C.

The inactivated pathogen can then be stored for prolonged periods (for example, for more than several months or more than 1 year). The solution containing the inactivated pathogen can then be administered directly to a subject for the purpose of eliciting an immune response against the pathogen, for example, as a vaccine. More commonly, the solution including the inactivated pathogen in the presence of hydrogen peroxide is lyophilized to produce an immunogenic composition. Lyophilization removes some, most or even all detectable hydrogen peroxide from the vaccine composition, and where desired produces a vaccine composition that is substantially free of hydrogen peroxide. Lyophilization can be performed by essentially any methods known in the art so long as the temperature is maintained below that at which heat denaturation of immunogenic epitopes occurs. Thus, the lyophilization can be performed following pre-freezing of the hydrogen peroxide/pathogen solution) or without pre-freezing (for example, at ambient temperatures above freezing, e.g., using a SPEED-VAC® concentrator under conditions that maintain the ambient temperature between about 0-4° C. and about 42° C.). For the purpose of manufacturing immunogenic compositions, such as vaccines, for administration to human or animal subjects, lyophilization is typically carried out according to approved good manufacturing procedures (GMP) for the production of vaccines.

The inactivation and lyophilization can be accomplished without any intervening processing step, such as dilution, dialization, centrifugation, or purification. So long as the pathogen/hydrogen peroxide solution is dispensed (or aliquoted) into clean, sterile containers (e.g., vial, ampules, tubes, etc.) prior to lyophilization, the resulting vaccine composition is sterile, and no additional preservative need be added prior to administration. For example, if the vaccine composition is to be administered in a single dose, the lyophilized vaccine composition is simply suspended (or dissolved) in a pharmaceutically acceptable diluent to produce a preservative-free liquid vaccine composition. In the event that the lyophilized vaccine composition is intended for multiple administrations (for example, multiple sequential administration to a single subject, or one or more administrations to multiple subjects) the diluent can include a pharmaceutically acceptable preservative.

The disclosure also relates to immunogenic (e.g., vaccine) compositions produced according to the methods disclosed herein. For example, in an embodiment, the composition (e.g., the medicament) is a lyophilized composition including an inactivated pathogen that retains one or more predominant antigenic epitope of the biologically active pathogen. Typically, the composition is substantially or completely free of any preservative or inactivating agent, such as formaldehyde or betapropiolactone. In another embodiment, the composition is a liquid produced by suspending or dissolving (solubilizing) the lyophilized composition in a pharmaceutically acceptable diluent. Optionally, the diluent contains a preservative. Optionally, the vaccine composition includes an adjuvant. In lyophilized form, the adjuvant can be, for example, an aluminum (e.g., alum or an aluminum salt) adjuvant. Upon preparation of a liquid formulation from the lyophilized vaccine composition, the adjuvant can be a lipid formulation e.g., an oil capable of forming an emulsion. The inactivated pathogen can be a virus, a bacterium, a fungus or a parasite (e.g., a protozoan parasite).

The disclosure also relates to methods of eliciting an immune response against a pathogen by administering the immunogenic compositions. Typically, the immune response is a protective immune response that prevents or reduces infection by one or more pathogens. For example, an immune response can be elicited in a subject by preparing a composition by contacting a pathogen with a solution containing an oxidizing agent such as hydrogen peroxide for a period sufficient to render the pathogen noninfectious; and administering the composition to a subject, thereby eliciting in the subject an immune response (e.g., a protective immune response) against the pathogen. In some applications the solution is administered to a subject without removing the hydrogen peroxide from the solution. In other applications, the composition is lyophilized, removing some or all (or substantially all) of the hydrogen peroxide. The lyophilized composition can be administered in powder form (for example, as a dispersed powder or as a pellet, e.g., using the POWDERJECT® transdermal powder injection device). Alternatively, the lyophilized composition is reconstituted in a pharmaceutically acceptable diluent for administration using any method suitable for delivering a vaccine to a subject, e.g., intramuscular, intradermal, transdermal, subcutaneous or intravenous injection, oral delivery, or intranasal or other mucosal delivery of the immunogenic composition (e.g., vaccine).

TERMS

Unless otherwise explained, all technical and scientific terms used herein have the same meaning as commonly understood by one of ordinary skill in the art to which this disclosure belongs. Definitions of common terms in molecular biology may be found in Benjamin Lewin, Genes V, published by Oxford University Press, 1994 (ISBN 0-19-854287-9); Kendrew et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8).

The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Additionally, numerical limitations given with respect to concentrations or levels of a substance, such as a growth factor, are intended to be approximate. Thus, where a concentration is indicated to be at least (for example) 200 pg, it is intended that the concentration be understood to be at least approximately (or "about" or "~") 200 pg.

Although methods and materials similar or equivalent to those described herein can be used in the practice or testing of this disclosure, suitable methods and materials are described below. The term "comprises" means "includes." The abbreviation, "e.g." is derived from the Latin exempli gratia, and is used herein to indicate a non-limiting example. Thus, the abbreviation "e.g." is synonymous with the term "for example."

In order to facilitate review of the various embodiments of this disclosure, the following explanations of specific terms are provided:

A "an immunogenic composition" or "vaccine composition" or "vaccine" is a composition of matter suitable for administration to a human or animal subject that is capable of eliciting a specific immune response, e.g., against a pathogen. As such, an immunogenic composition or vaccine includes one or more antigens or antigenic epitopes. The antigen can be in the context of an isolated protein or peptide fragment of a protein, or can be a partially purified preparation derived from a pathogen. Alternatively, the antigen can be in the context of a whole live or inactivated pathogen. Typically, when an immunogenic composition or vaccine includes a live pathogen, the pathogen is attenuated, that is, incapable of causing disease in an immunologically competent subject. In other cases, an immunogenic composition or vaccine includes a whole inactivated (or killed) pathogen. The inactivated pathogen can be either a wild-type pathogenic organism that would otherwise (if not inactivated) cause disease in at least a portion of immunologically competent subjects, or an attenuated or mutant strain or isolate of the pathogen. In the context of this disclosure, the immunogenic and/or vaccine compositions contain a whole (wild-type, attenuated or mutant) pathogen.

An "immune response" is a response of a cell of the immune system, such as a B cell, T cell, or monocyte, to a stimulus. In some cases, an immune response is a T cell response, such as a CD4+ response or a CD8+ response. Alternatively, the response is a B cell response, and results in the production of specific antibodies. In some cases, the response is specific for a particular antigen (that is, an "antigen-specific response"). If the antigen is derived from a pathogen, the antigen-specific response is a "pathogen-specific response." A "protective immune response" is an immune response that inhibits a detrimental function or activity of a pathogen, reduces infection by a pathogen, or decreases symptoms (including death) that result from infection by the pathogen. A protective immune response can be measured, for example, by the inhibition of viral replication or plaque formation in a plaque reduction assay or ELISA-neutralization assay, or by measuring resistance to viral challenge in vivo.

An "immunologically effective amount" is a quantity of a composition used to elicit an immune response in a subject. In the context of a vaccine administration, the desired result is typically a protective pathogen-specific immune response. However, to obtain protective immunity against a pathogen in an immunocompetent subject, multiple administrations of the vaccine composition are commonly required. Thus, in the context of this disclosure, the term immunologically effective amount encompasses a fractional dose that contributes in combination with previous or subsequent administrations to attaining a protective immune response.

An "antigen" is a compound, composition, or substance that can stimulate the production of antibodies and/or a T cell response in an animal, including compositions that are injected, absorbed or otherwise introduced into an animal. The term "antigen" includes all related antigenic epitopes. The term "epitope" or "antigenic determinant" refers to a site on an antigen to which B and/or T cells respond.

The "predominant antigenic epitopes" are those epitopes to which a functionally significant host immune response, e.g., an antibody response or a T-cell response, is made. Thus, with respect to a protective immune response against a pathogen, the predominant antigenic epitopes are those antigenic moieties that when recognized by the host immune system result in protection from disease caused by the pathogen.

An "adjuvant" is an agent that enhances the production of an immune response in a non-specific manner. Common adjuvants include suspensions of minerals (alum, aluminum hydroxide, aluminum phosphate) onto which antigen is adsorbed; or water-in-oil emulsion in which an antigen solution is emulsified in oil (MF-59, Freund's incomplete adjuvant). Additional details regarding various adjuvants can be found in Derek O'Hagan Vaccine Adjuvants: Preparation Methods and Research Protocols (Methods in Molecular Medicine) Humana Press, 2000.

The term "whole pathogen" refers to a pathogenic organism, such as a virus, a bacterium, a fungus or a parasite, that includes all or substantially all of the constituents of the infectious form of the organism. Typically, a whole pathogen is capable of replication. The term "whole pathogen" is nonetheless distinct from the term "wild-type" pathogen, and the term "whole pathogen" encompasses wild-type as well as attenuated and other mutant forms of the pathogenic organism. Thus, a whole pathogen can be an attenuated pathogen incapable of causing disease in an immunocompetent host, but nonetheless including all or substantially all of the constituents of an infectious pathogen. Similarly, a whole pathogen can be a mutant form of the pathogen, lacking one or more intact (wild-type) genes, and/or proteins.

An "inactivated pathogen" is a whole pathogen that has been rendered incapable of causing disease (e.g., rendered noninfectious) by artificial means. Typically, an inactivated pathogen is a "killed pathogen" that is incapable of replication. A pathogen is noninfectious when it is incapable of replicating or incapable of replicating to sufficient levels to cause disease.

An "immunogenically active pathogen" is a pathogen that is capable of eliciting an immune response when introduced into an immunologically competent subject. The immune response produced in response to exposure to an immunogenically active pathogen is identical with respect to the predominant antigenic epitopes to that produced by the infectious pathogen.

An "oxidizing agent" is any agent that contributes oxygen, extracts hydrogen, and/or extracts electrons in a reaction. The strength of an oxidizing agent can be determined based on its standard electrode potential, with the strongest oxidizing agents having the highest standard potential (in volts). Hydrogen peroxide ($H_2O_2$) is an exemplary oxidizing agent with a standard electrode potential of 1.78 volts.

A "solution comprising hydrogen peroxide" includes the combination of any mixture of a solvent and hydrogen peroxide, containing more a than trace amount of hydrogen peroxide. For example, a hydrogen peroxide solution can include 0.01% hydrogen peroxide, 0.05%, 0.1% or more hydrogen peroxide. Solutions including up to 90% or more hydrogen peroxide can be produced, but are highly unstable. Commercially available hydrogen peroxide solutions typically do not exceed about 35% hydrogen peroxide. Most commonly, in the context of the methods disclosed herein the solvent is water, e.g., deionized water, or an aqueous buffered salt solution. Typically, the term solution includes liquid phase solutions and vapor phase solutions containing hydrogen peroxide. For purpose of consistency, the proportion of hydrogen peroxide in a solution is given as weight per volume (wt/vol).

The phrase "substantially free of hydrogen peroxide" indicates that no more than trace amounts (amounts empirically detectable as background) are present in the composition.

The verb "lyophilize" means to freeze-dry under vacuum. The process is termed "lyophilization." In some cases, the sample to be dried (e.g., dehydrated) is frozen prior to drying. In other cases, the material to be dried is subjected to the drying process without prior phase change. During the process of lyophilization, evaporation of the solvent results in cooling of the sample to temperatures below the melting temperature of the solvent/solute mixture resulting in freezing of the sample. Solvent is removed from the frozen sample by sublimation. A product that has undergone lyophilization is "lyophilized." As used in this disclosure the term lyophilization also encompasses functionally equivalent procedures that accelerate the drying process without exposing the sample to excessive heat, specifically including: spray drying and spray freeze-drying.

In the context of this disclosure "room temperature" refers to any temperature within a range of temperatures between about 16° C. (approximately 61° F.) and about 25° C. (approximately 77° F.). Commonly, room temperature is between about 20° C. and 22° C. (68° F.-72° F.). Generally, the term room temperature is used to indicate that no additional energy is expended cooling (e.g., refrigerating) or heating the sample or ambient temperature.

A "preservative" is an agent that is added to a composition to prevent decomposition due to chemical change or microbial action. In the context of vaccine production, a preservative is typically added to prevent microbial (e.g., bacterial and fungal) growth. The most common preservative used in vaccine production is thimerosal, a mercury containing organic compound. Thus, the term "preservative-free" indicates that no preservative is added to (or present in) the composition.

The term "purification" (e.g., with respect to a pathogen or a composition containing a pathogen) refers to the process of removing components from a composition, the presence of which is not desired. Purification is a relative term, and does not require that all traces of the undesirable component be removed from the composition. In the context of vaccine production, purification includes such processes as centrifugation, dialization, ion-exchange chromatography, and size-exclusion chromatography, affinity-purification or precipitation.

The adjective "pharmaceutically acceptable" indicates that the subject is physiologically acceptable for administration to a subject (e.g., a human or animal subject). Remington's Pharmaceutical Sciences, by E. W. Martin, Mack Publishing Co., Easton, Pa., 15th Edition (1975), describes compositions and formulations (including diluents) suitable for pharmaceutical delivery of therapeutic and/or prophylactic compositions, including vaccines.

In general, the nature of the diluent will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. In certain formulations (for example, solid compositions, such as powder, pill, tablet, or capsule forms), a liquid diluent is not employed. In such formulations, non-toxic solid carriers can be used, including for example, pharmaceutical grades of mannitol, lactose, starch or magnesium stearate.

The phrase "Good Manufacturing Practice" or "GMP" with respect to methods and procedures employed in vaccine production refer specifically to the set of methods, protocols and procedures established by the United States Food and Drug Administration (FDA). Similar recommendations and guidelines are promulgated by the World Health Organization. The abbreviation "cGMP" specifically designates those protocols and procedures that are currently approved by the FDA (e.g., under 21 Code of Federal Regulations, parts 210 and 211, available on the world wide web at fda.gov/cder/dmpq). With time cGMP compliant procedures may change. Any methods disclosed herein can be adapted in accordance with new cGMP requirements as mandated by the FDA.

Inactivating Pathogens with Hydrogen Peroxide

The antimicrobial effects of hydrogen peroxide have been well established since at least the early 1960s, and hydrogen peroxide (e.g., hydrogen peroxide vapor) is used extensively for decontaminating surfaces in manufacturing and medical/surgical applications. Nonetheless, the utility of hydrogen peroxide in the context of vaccine production has not previously been recognized. Inactivation of pathogens with hydrogen peroxide provides several advantages over other methods of vaccine production from live pathogens. Foremost among these is the preservation of antigenic epitopes. Unlike methods that use formaldehyde, propiolactone, ultraviolet irradiation, and/or heat to inactivate live pathogens, inactivation with hydrogen peroxide does not result in the destruction (e.g., by cross-linking, alkylation or denaturation) of antigenic epitopes. Thus, the methods described herein enable the production of vaccine compositions containing inactivated pathogens that retain the immunologic properties of the live pathogen, providing a more immunologically effective (immunogenic) vaccine composition.

While neither ultraviolet irradiation or heat inactivation leave any toxic or carcinogenic residue following inactivation, both result in significant denaturation of antigenic epitopes, reducing the efficacy of the antigenic preparation. In addition, ultraviolet irradiation is extremely sensitive to the quality of the pathogen preparation, as UV light is unable to penetrate dense solutions, especially those containing particulate matter such as aggregates of pathogen formed during the preparation process. This incomplete penetration makes the process too unreliable for routine vaccine production.

Formaldehyde and propiolactone can be used with consistent results to obtain complete inactivation of a variety of pathogens. However, both of these agents leave behind toxic and carcinogenic contaminants, which have been shown to be detrimental to human health.

Because hydrogen peroxide is well tolerated by human and animal subjects in low concentrations (concentrations less than about 3% or 1%, or less), the inactivated pathogen can be administered directly to a subject (e.g., subcutaneously, intraperitoneally, or intravenously) without further processing without significant adverse physiological effects. Indeed, in some animal applications, an inactivated pathogen is simply administered in the solution of hydrogen peroxide utilized to inactivate the pathogen.

Although human subjects also tolerate hydrogen peroxide well, there is evidence that hydrogen peroxide has adverse physiological effects on new cell growth. Therefore, particularly in applications involving administration of the inactivated pathogen to a human subject, it is typically desirable to substantially completely remove the hydrogen peroxide from the vaccine composition. This can be done simply and effectively by lyophilizing the solution to remove the hydrogen peroxide. However, in contrast to other chemical inactivating agents, such as formaldehyde and propiolactone, no additional purification steps are required to remove the hydrogen peroxide prior to subsequent processing, and no toxic contaminants remain in the lyophilized vaccine composition if further processing to remove the inactivating agent is not performed. This greatly simplifies vaccine production and cost of manufacturing. Lyophilization procedures are discussed in greater detail herein below. Alternatively, the hydrogen peroxide can be removed by dialysis.

For direct administration purposes and/or when subsequent processing does not immediately (temporally) follow inactivation, the inactivated pathogen can be stored frozen in the hydrogen peroxide solution for long periods of time (for example, longer than 3 months, longer than 1 year) without loss of immunogenic activity.

Another benefit of using hydrogen peroxide to inactivate pathogens is the low cost and ease of use. High quality reagent grade hydrogen peroxide is available commercially as a 30% (typically 29-32%) solution. Although precautions must be taken in storing bulk hydrogen peroxide because concentrated hydrogen peroxide is a strong oxidizing agent that can is combustible and/or explosive when contacted with fire, 30% hydrogen peroxide poses little risk to personnel when used with reasonable care to prevent inhalation of large amounts of vapor or direct contact with skin and eyes. Contact with skin, eyes and respiratory tract can cause irritation, which can generally be treated by flushing or washing thoroughly with clean water. When used in lower concentrations (e.g., at or less than about 0.1-10%) hydrogen peroxide poses little health risk.

Although the compositions and methods disclosed herein are described with particular reference to hydrogen peroxide, it will be appreciated by those of skill in the art, that other oxidizing agents can also be used to inactivate pathogens for the purpose of producing immunogenic composition, such as vaccines, as disclosed herein. Examples of additional oxidizing agents with their standard electrode potentials are shown in Table 1. The use of additional oxidizing agents proceeds essentially as described herein with respect to hydrogen peroxide, with the exception that appropriate precautions are taken to ensure the safe handling of the particular oxidizing agent. In general, when preparing immunogenic compositions such as vaccines, it is desirable to select an oxidizing agent that produces only water and a diffusible gas as products. Examples of such oxidizing agents include (in addition to hydrogen peroxide): $O_2$, $O_3$, and $NO_3^-$. It will be appreciated that other oxidizing agents can be used in the production of immunogenic compositions, however, removal of by-products may involve additional processing steps. For example, in certain instances the oxidizing reagent produces a solid by-product that can be removed by, e.g., filtration or centrifugation.

TABLE 1

Standard Electrode Potentials of Exemplary Oxidizing Agents
Standard Electrode Potentials in Aqueous Solution at 25° C.

| Cathode (Reduction) Half-Reaction | Standard Potential E° (volts) |
|---|---|
| $Sn^{4+}(aq) + 2e^- \rightarrow Sn^{2+}(aq)$ | 0.15 |
| $Cu^{2+}(aq) + e^- \rightarrow Cu^+(aq)$ | 0.16 |
| $ClO_4^-(aq) + H_2O(l) + 2e^- \rightarrow ClO_3^-(aq) + 2OH^-(aq)$ | 0.17 |
| $AgCl(s) + e^- \rightarrow Ag(s) + Cl^-(aq)$ | 0.22 |
| $Cu^{2+}(aq) + 2e^- \rightarrow Cu(s)$ | 0.34 |
| $ClO_3^-(aq) + H_2O(l) + 2e^- \rightarrow ClO_2^-(aq) + 2OH^-(aq)$ | 0.35 |
| $IO^-(aq) + H_2O(l) + 2e^- \rightarrow I^-(aq) + 2OH^-(aq)$ | 0.49 |
| $Cu^+(aq) + e^- \rightarrow Cu(s)$ | 0.52 |
| $I_2(s) + 2e^- \rightarrow 2I^-(aq)$ | 0.54 |
| $ClO_2^-(aq) + H_2O(l) + 2e^- \rightarrow ClO^-(aq) + 2OH^-(aq)$ | 0.59 |
| $Fe^{3+}(aq) + e^- \rightarrow Fe^{2+}(aq)$ | 0.77 |
| $Hg_2^{2+}(aq) + 2e^- \rightarrow 2Hg(l)$ | 0.80 |
| $Ag^+(aq) + e^- \rightarrow Ag(s)$ | 0.80 |
| $Hg^{2+}(aq) + 2e^- \rightarrow Hg(l)$ | 0.85 |
| $ClO^-(aq) + H_2O(l) + 2e^- \rightarrow Cl^-(aq) + 2OH^-(aq)$ | 0.90 |
| $2Hg^{2+}(aq) + 2e^- \rightarrow Hg_2^{2+}(aq)$ | 0.90 |
| $NO_3^-(aq) + 4H^+(aq) + 3e^- \rightarrow NO(g) + 2H_2O(l)$ | 0.96 |
| $Br_2(l) + 2e^- \rightarrow 2Br^-(aq)$ | 1.07 |
| $O_2(g) + 4H^+(aq) + 4e^- \rightarrow 2H_2O(l)$ | 1.23 |
| $Cr_2O_7^{2-}(aq) + 14H^+(aq) + 6e^- \rightarrow Cr^{3+}(aq) + 7H_2O(l)$ | 1.33 |
| $Cl_2(g) + 2e^- \rightarrow 2Cl^-(aq)$ | 1.36 |
| $Ce^{4+}(aq) + e^- \rightarrow Ce^{3+}(aq)$ | 1.44 |
| $MnO_4^-(aq) + 8H^+(aq) + 5e^- \rightarrow Mn^{2+}(aq) + 4H_2O(l)$ | 1.49 |
| $H_2O_2(aq) + 2H^+(aq) + 2e^- \rightarrow 2H_2O(l)$ | 1.78 |
| $Co^{3+}(aq) + e^- \rightarrow Co^{2+}(aq)$ | 1.82 |
| $S_2O_8^{2-}(aq) + 2e^- \rightarrow 2SO_4^{2-}(aq)$ | 2.01 |
| $O_3(g) + 2H^+(aq) + 2e^- \rightarrow O_2(g) + H_2O(l)$ | 2.07 |
| $F_2(g) + 2e^- \rightarrow 2F^-(aq)$ | 2.87 |

To inactivate a pathogen using hydrogen peroxide, the live pathogen is grown to a desired density (e.g., saturation density in culture), according to any procedures acceptable in the art for growing (e.g., culturing the specific organism). Typically, for cellular pathogens, it is desirable to culture the pathogen to stationary phase; as such organisms are generally more resistant to stresses in subsequent processing than those harvested at logarithmic phase. Growth in culture can be monitored using methods known in the art, such as measuring optical density of the culture using spectrophotometry. When the pathogen is a virus, growth can monitored by titering the virus using standard methods established for the selected virus. For example, methods for growing animal viruses can be found, for example, in DNA Viruses: A Practical Approach, Alan J. Cann (ed.) Oxford University Press, 2000; Robinson and Cranage (eds.) Vaccine Protocols (Methods in Molecular Medicine) Humana Press, 2003, and references cited therein. Methods for culturing pathogenic bacteria are also known in the art, and can be found in Molecular Cloning: A Laboratory Manual, 2nd ed., vol. 1-3, ed. Sambrook et al., Cold Spring Harbor Laboratory Press, Cold Spring Harbor, N.Y., 1989. Methods for culturing parasites, such as malaria, are also known in the art, e.g., Denise Doolan (ed.) Malaria Methods and Protocols (Methods in Molecular Medicine) Humana Press, 2002, and references cited therein.

Typically, the pathogenic organisms (e.g., viruses, bacteria, fungus, or parasites) are purified from the medium in which they are grown or cultured, and in the case of pathogens that replicate inside a cell are purified from the other cellular components. For example, the relative concentration of non-pathogen components of a suspension including pathogens can be decreased by at least 50%, such as about 70%, or by as much as 80%, or even by 90%, 95% or more, relative to a crude preparation of pathogen. Intracellular pathogens, such as viruses, can be isolated or purified from the various components of the cells they infect by various methods known in the art.

For example, viruses for vaccine production are typically grown under controlled conditions in a certified cell line using biologically and chemically defined culture medium according to cGMP procedures. Cells are usually infected with virus at an appropriate multiplicity of infection (MOI), and the cells are maintained in culture under conditions and for a period of time sufficient to permit replication of the virus to high titer. The cells are then harvested by centrifugation (following release from the culture surface in the case of adherent cells), and resuspended in an appropriately buffered solution. To facilitate recovery, the buffered solution is typically hypotonic with respect to the cells, causing the cells to swell. Optionally, the cell suspension is agitated periodically to ensure a more uniform exposure of the cells to the hypotonic solution. The cells are then lysed, for example, by homogenization, to release the virus. The lysate is centrifuged to remove large particulate matter, such as cell nuclei, and the supernatant is filtered to remove additional cellular debris. The virus can then be further purified by layering the filtered supernatant onto a suitable separation medium, such as s sucrose. Optionally, the nuclear pellet can be further processed to increase viral yield. The nuclear pellet is resuspended again in hypotonic buffer and homogenized. The nuclear lysate is centrifuged and the resulting supernatant is filtered prior to layering onto separation medium. Optionally, the two viral suspensions are combined to achieve an approximately equal volume separation gradient. The separation medium/virus suspension is then processed by ultracentrifugation (e.g., at 55,000×g for 1-1.5 hours at 4° C. Virus is collected into a pellet by this process whereas membranous cellular debris remains at the interface. The supernatant is removed (typically by aspiration) and the pellet is resuspended in buffer. The purified virus can then be evaluated for recovery and viability (for example by determining protein concentration and by plaque assays, respectively). If desired the recovered virus can be frozen and stored until use.

Similar procedures are known in the art for purifying non-viral pathogens, such as intracellular parasites (for example, protozoan parasites, including *Plasmodium falciparum* and other *Plasmodium* species, *Leishmania* (sp.), *Cryptosporidium parvum, Entamoeba histolytica*, and *Giardia lamblia*, as well as *Toxoplasma, Eimeria, Theileria*, and *Babesia* species).

Following purification, the pathogen can be resuspended in a convenient volume of solution, such as water or another aqueous (for example, pharmaceutically acceptable) carrier solution, such as a dilute or physiological salt solution. Hydrogen peroxide is added to the solution to inactivate the pathogen. Optionally, the pathogens can be resuspended directly into a hydrogen peroxide solution. Alternatively, hydrogen peroxide can be added directly to the culture medium without prior purification of the pathogen. The latter method can be desirable to render highly pathogenic organisms safer (less infectious) during the production process. The hydrogen peroxide can be removed by lyophilization or by dialysis, or by various chromatography methods as described above. Similarly, where medium components or other contaminants that are not desired in the final vaccine preparation remain in the solution, such components can be removed using procedures known in the art, e.g., as described above. Salts, sugars and other buffer or medium components are not typically immunogenic, and many such components are consistent with FDA approved formulations. In such cases, there is no need to remove these components from the preparation. In some cases, defined salts or sugars (or other stabilizers) can be added to stabilize lyophilized compositions. Hydrogen peroxide is compatible with a number of vaccine stabilizers (sucrose, dextrose, gelatin, albumin, etc.) used in the industry and recognized as common in the art. The specific formulations that are optimal for each pathogen can be determined empirically by one of ordinary skill in the art.

The inactivating solution contains an amount of hydrogen peroxide sufficient to render all of the pathogens noninfectious. Depending on the density of the organisms in the final solution, and the type of organism, the amount of hydrogen peroxide can vary. Generally, the solution contains at least about 0.03% hydrogen peroxide. More commonly, the solution includes at least about 0.1%, such as at least about 0.5% hydrogen peroxide. Typically, the solution contains at least about 1% hydrogen peroxide. Because it is readily available commercially, often the solution contains about 3% hydrogen peroxide. Nonetheless, the solution can include as much as 30% hydrogen peroxide, for example, about 5%, or about 10%, or about 20% hydrogen peroxide. Reagent grade hydrogen peroxide suitable for use in vaccine preparation is available in a 30% solution. Thus, although it is possible to use concentrations exceeding 30% there is little practical value, and some practical inconvenience in doing so. Complete inactivation of most pathogens can be achieved at concentrations between 0.03% and 5%, so there is little practical advantage in using a solution that exceeds about 3% hydrogen peroxide.

The pathogen is maintained (e.g., incubated) in contact with the hydrogen peroxide for a period of time sufficient to inactivate all of the pathogen in the sample. In general, the length of time in the inactivating solution is inversely correlated with the concentration of hydrogen peroxide in the solution. For example, a selected pathogen can be inactivated in a 3% hydrogen peroxide solution for a shorter period of time as compared to the period required in a 0.03% solution. The period of time and concentration of hydrogen peroxide can be determined empirically for any pathogen. For example, performing the inactivation in a solution containing 3% hydrogen peroxide for a period of approximately 2 hours at room temperature assures complete (100%) inactivation of a broad range of pathogens.

While the precise temperature is not important, it is generally desirable to maintain the solution at a temperature that is below the temperature at which heat denaturation of antigenic epitopes begins. Thus, it is generally preferred to maintain the solution at a temperature above 0° C. and below about 42° C. Most commonly, the inactivation is performed at room temperature or at approximately 4° C. It will be appreciated by those of ordinary skill in the art that inactivation of pathogens using hydrogen peroxide is effective over a wide range of conditions, any of which provide complete inactivation of a pathogen of interest. Typically, the conditions are selected for the sake of convenience from among those conditions giving complete inactivation.

Although it is generally most convenient to simply suspend the selected pathogen in a solution containing an appropriate amount of hydrogen peroxide for a period sufficient to effect complete inactivation of the pathogen, alternative methods for contacting a pathogen with a solution containing hydrogen peroxide are available. These are encompassed within the disclosed methods. For example, $H_2O_2$ solution can be produced by percolating $O_2$ or $O_3$ through an aqueous solution that includes a hydrogen donor.

Hydrogen peroxide vapor sterilizers can also be used to inactivate pathogens for production of immunogenic compositions. Hydrogen peroxide vapor sterilizers are available commercially. This type of apparatus is designed for the economical sterilization of surfaces, e.g., in the context of clean room production facilities, and in surgical and medical settings. Although the means of producing the vapor varies somewhat from apparatus to apparatus, a hydrogen peroxide vapor sterilizer produces a vapor from a concentrated (e.g., 30%) hydrogen peroxide solution, and are available from, e.g., BioQuell, Pharmaceutical Systems, Inc. (VHYPER™), and Advanced Sterilization Products (STERRAD®). When using such devices the parameters are set to insure that the temperature does not exceed about 42° C. to prevent heat denaturation of predominant antigenic epitopes during inactivation.

Although some pathogens can be activated in vapor phase by projecting an aerosol containing the pathogen through the vapor phase hydrogen peroxide, more commonly, the pathogen to be inactivated is placed on (or adsorbed, adhered or otherwise immobilized) onto a solid surface where it is exposed to hydrogen peroxide vapor. Essentially any solid surface is suitable as a substrate for hydrogen peroxide inactivation of pathogens. For example, tissue culture plates or dishes, including microtiter plates, as well as pins, beads, or membranes can be used to provide a solid surface on which to expose a pathogen to hydrogen peroxide vapor. Typically, the solid surface is selected based on compatibility with the processing steps undertaken to recover the pathogen for vaccine production. For example, in vaccine preparation processes that involve filtration or centrifugation of the pathogen through a membrane (or filter), the membrane can be removed from the centrifugation or filtration device and exposed to hydrogen peroxide vapor to inactivate the pathogen collected on the membrane. In other cases, for example, where the vaccine composition includes the pathogen adhered to a carrier, the pathogen is exposed to hydrogen peroxide vapor on the carrier. Suitable carriers for vaccine formulation include biodegradable microspheres, such as poly (lactic/glycolic) acid (PLGA) microspheres.

Lyophilization of Inactivated Pathogens

Following inactivation in low concentrations (up to about 10%, for example, between 0.03% and about 3%) of hydrogen peroxide, the inactivated pathogen can be stored (for example, frozen in solution) or administered to a subject without further processing. Nonetheless, for most uses, especially administration to human subjects, it is desirable to prepare unit doses in a form convenient for distribution. To do this, and to remove the hydrogen peroxide from the vaccine composition, the solution can be lyophilized. Lyophilization under suitable conditions and formulations results in an immunogenic composition (e.g., a vaccine) that is stable for long periods of time at between 4° C. and room temperature (depending on the pathogen), and which can be easily and economically distributed world-wide using the existing transportation infrastructure. Procedures for lyophilizing vaccine compositions are well known in the art, and explained in additional detail in, e.g., U.S. Pat. Nos. 3,932,943; 4,134,214; 4,710,378; 4,622,222; 6,562,350; and 6,884,422, the disclosures of which are incorporated herein by reference.

Lyophilization is performed when a solvent/solute mixture is subjected to vacuum resulting in the sublimation of the solvent, and leaving behind the dried solute(s). Typically a vacuum of at least about 0.5 mBar is sufficient to promote efficient sublimation. Although the pressure can be further reduced, doing so has little effect on drying rate, and under very low pressure conditions, efficiency of sublimation is decreased. For vaccine production, it is often convenient to lyophilize the pathogen sample in receptacles suitable for distribution and administration (for example, in single doses or a small number of multiple doses). Most commonly, the receptacle is a glass vial, which can be sealed with a rubber stopper. Such vials are readily available in 2 ml, 3 ml, 5 ml and 10 ml volumes, although any volume can be utilized. Alternative receptacle formats can also be used, including for example, glass ampoules, and syringes (for example, see U.S. Pat. No. 6,605,064, the disclosure of which is incorporated herein by reference). Additionally, the composition can be lyophilized without special regard to the receptacle and subsequently formulated for administration to a subject, e.g., in powder, tablet or pellet form. The optimal protocol for lyophilization can be determined empirically for each selected pathogen. The following provides general guidelines for the lyophilization of compositions containing inactivated pathogens.

Although lyophilization can be performed simply by placing a liquid sample into a vacuum chamber, this is not generally advisable in the context of vaccine preparation because it can result in "frothing" of the sample, which can result in damage to the antigen. To prevent frothing, a pathogen sample can be frozen prior to lyophilization. The method and rate of freezing depend on several considerations. Generally, a relatively slow cooling rate of between 0.1° C. and 1.0° C./minute is used to promote development of large ice crystals that are conducive to vapor migration. However, slow cooling rates are generally not optimal for cellular pathogens, such as bacteria, fungus and parasites. Under slow cooling conditions, the pathogen is exposed to increasing concentrations of solutes, including any salts and media components in the sample. Cells should therefore be cooled more rapidly to prevent prolonged exposure to solutes that might have an adverse effect on the pathogen. Cooling at very rapid rates is also detrimental because intracellular water is unable to diffuse, resulting in damage to the cells. Although rapid cooling can lead to the formation of small disorganized ice crystals that are suboptimal for lyophilization, this problem can be remedied by heat annealing the sample prior to lyophilization. Heat annealing is performed by warming and recooling the sample without allowing the sample to melt. Alternatively, additives, e.g., cryoprotectants, can be used to prevent damage to pathogen during freezing. Common pharmaceutically acceptable excipients that reduce damage during lyophilization include sucrose and other sugars, amino acids, such as threonine and cysteine, and surfactants, such as Tween.

As an alternative to prefreezing, the pathogen sample can be lyophilized with low-speed centrifugation. For example, lyophilization can be carried out in an apparatus, such as a SPEED-VAC® concentrator (Savant), which includes a centrifuge contained within a vacuum chamber attached to an exhaust system for removing the solvent vapor. In such an apparatus, lyophilization can be performed at an ambient temperature above freezing, so long as the sample is maintained throughout the process below the temperature at which heat denaturation of antigens occurs. For example, as discussed in the Examples, lyophilization can conveniently be performed at room temperature (or at 4° C.) in a SPEED-VAC® concentrator.

Following sublimation of the solvent the receptacle containing the inactivated pathogen can be sealed to maintain sterility before removal from the lyophilization apparatus. Most commonly, glass vials are sealed with rubber stoppers, which can be penetrated by an injection needle for withdrawal of the vaccine composition following reconstitution. One advantage of this system is that the vials can be sealed without releasing the vacuum assuring integrity of the sample. Glass ampoules are typically sealed following release of the vacuum. To preserve integrity of the seal, and prevent introduction of ambient air, the vial can be filled with a sterile gas, such as argon or nitrogen prior to sealing. Inert gasses, such as argon can provide enhanced stability as compared to nitrogen, if it is expected that the vaccine composition will be stored for prolonged periods of time.

Lyophilization provides a convenient, adaptable means of producing a stable, sterile composition in the context of commercial manufacture. Nonetheless, for certain applications, alternative methods are warranted. Such methods are also suitable for processing pathogens inactivated using a solution containing hydrogen peroxide. For example, in applications where an antigen is to be administered in combination with an alum-hydrogel adjuvant, lyophilization is not appropriate because the structure responsible for increased immunogenicity is disrupted by lyophilization. In such cases, alternative methods, such as freeze-spray drying can be preferable. Freeze-spray drying can be performed by spraying the pathogen conjugated alum-gel into liquid nitrogen.

Reconstitution and Administration

Immunogenic compositions, such as vaccines, that are produced as lyophilized powders are typically mixed with a liquid for administration. This process is known as "reconstitution," and the liquid used is commonly referred to as a "diluent." For purposes of administration, especially to human subjects, it is important that the diluent be a pharmaceutically acceptable formulation. Reconstitution of the lyophilized composition is typically carried out using a sterile syringe and needle for each vial of diluent. The correct diluent for each type and batch is used to ensure adequate potency, safety and sterility of the resulting mixture. Diluents are specifically designed to optimize delivery and efficacy of the selected composition. Common diluents include such additives as: stabilizers to improve heat stability of the vaccine; agents, such as surfactants, to assist in dissolving the powder into a liquid; and buffers to ensure the correct acidic balance of the reconstituted composition. Optionally, the diluent can contain a preservative (e.g., a bactericide and/or a fungicide) to maintain sterility after reconstitution. Preservatives are typically required (e.g., by the FDA) when the composition is reconstituted in a multi-dose formulation.

Administration of Immunogenic Compositions Such as Vaccines (Therapeutic Methods)

The immunogenic compositions (such as vaccine or other medicaments) disclosed herein can be administered to a subject to elicit an immune response against a pathogen. Most commonly, the compositions are administered to elicit a prophylactic immune response against a pathogenic organism to which the subject has not yet been exposed. For example, vaccine compositions including hydrogen peroxide-inactivated pathogens can be administered as part of a localized or wide-spread vaccination effort. An immune response elicited by administration of the such vaccine compositions typically includes a neutralizing antibody response, and can in addition include a T cell response, e.g., a cytotoxic T cell response that targets cellular pathogens. Accordingly, methods for making a medicament or pharmaceutical composition containing hydrogen peroxide-inactivated pathogens are included herein. The pharmaceutical compositions (medicaments) include at least one pathogen inactivated by contact with a solution containing hydrogen peroxide, in a pharmaceutically acceptable carrier or excipient.

In some cases, the immunogenic composition can include a combination of pathogens, such as a combination of viruses (for example mumps virus, measles virus, rubella virus), or a combination of bacteria (for example, *Corynebacterium diptheriae*, *Bordatella pertussis* and *Clostridium tetani*), or a combination of pathogens selected from different classes of organisms (e.g., one or more viruses and one or more bacteria, one or more bacteria and one or more parasites, and the like).

The quantity of pathogen included in the composition is sufficient to elicit an immune response when administered to a subject. For example, when administered to a subject in one or more doses, a vaccine composition containing an inactivated pathogen favorably elicits a protective immune response against the pathogen. A dose of the vaccine composition can include at least about 0.1% wt/wt inactivated pathogen to about 99% wt/wt inactivated pathogen, with the balance of the vaccine composition is made up of pharmaceutically acceptable constituents, such as a pharmaceutically acceptable carrier and/or pharmaceutically acceptable diluent. Guidelines regarding vaccine formulation can be found (e.g., in U.S. Pat. Nos. 6,890,542, and 6,651,655). In one specific, non-limiting example the vaccine composition (medicament) includes at least about 1%, such as about 5%, about 10%, about 20%, about 30% or about 50% wt/wt inactivated pathogen. As will be apparent to one of ordinary skill in the art, the quantity of pathogen present in the vaccine formulation depends on whether the composition is a liquid or a solid. The amount of inactivated pathogen in a solid composition can exceed that tolerable in a liquid composition. The amount of inactivated pathogen can alternatively be calculated with respect to the comparable amount of a live or inactivated pathogen required to give an immune response. For example, a dosage equivalent in viral particles to from about $10^6$ to about $10^{12}$ plaque forming units (PFU) of live or attenuated virus can be included in a dose of the vaccine composition. Similarly, a vaccine composition can include a quantity of inactivated bacteria, fungus or parasite equivalent to between about $10^3$ to about $10^{10}$ live organisms. Alternatively, the dosage can be provided in terms of protein content or concentration. For example, a dose can include from approximately 0.1 µg, such as at least about 0.5 µg protein. For example, a dose can include about 1 µg of an isolated or purified virus or other pathogen up to about 100 µg, or more of a selected pathogen. Although the equivalent doses in infectious units (e.g., PFU) can vary from pathogen to pathogen, the appropriate protein dose can be extrapolated (for example, from PFU) or determined empirically. For example, in a typical preparation, 1 µg of purified vaccinia virus is equivalent to approximately $2 \times 10^6$ PFU. Similar conversions can be determined for any pathogen of interest.

Typically, preparation of a vaccine composition (medicament) entails preparing a pharmaceutical composition that is essentially free of pyrogens, as well as any other impurities that could be harmful to humans or animals. Typically, the pharmaceutical composition contains appropriate salts and buffers to render the components of the composition stable and allow for presentation of the peptides by antigen presenting cells. Such components can be supplied in lyophilized form, or can be included in a diluent used for reconstitution of a lyophilized form into a liquid form suitable for administration. Alternatively, where the inactivated pathogen is prepared for administration in a solid state (e.g., as a powder or pellet), a suitable solid carrier is included in the formulation.

Aqueous compositions typically include an effective amount of the inactivated pathogen dispersed (for example, dissolved or suspended) in a pharmaceutically acceptable diluent or aqueous medium. The phrase "pharmaceutically acceptable" refers to molecular entities and compositions that do not produce an adverse, allergic or other undesirable reaction when administered to a human or animal subject. As used herein, "pharmaceutically acceptable carrier" includes any and all solvents, dispersion media, coatings, isotonic and absorption delaying agents and the like. Optionally, a pharmaceutically acceptable carrier or diluent can include an antibacterial, antifungal or other preservative. The use of such media and agents for pharmaceutically active substances is well known in the art. Except insofar as any conventional media or agent is incompatible with production of an immune response by an inactivated pathogen, its use in the immunogenic compositions is contemplated. Supplementary active ingredients also can be incorporated into the compositions. For example, certain pharmaceutical compositions can include the inactivated pathogen in an aqueous diluent, mixed with a suitable surfactant, such as hydroxypropylcellulose. Dispersions also can be prepared in glycerol, liquid polyethylene glycols, and mixtures thereof and in oils. In some cases (for example, when liquid formulations are deemed desirable, or when the lyophilized vaccine composition is reconstituted for multiple doses in a single receptacle), these preparations contain a preservative to prevent the growth of microorganisms.

Pharmaceutically acceptable carriers, excipients and diluents are known to those of ordinary skill in the described, e.g., in Remington's Pharmaceutical Sciences, by E. W. Martin, Mack Publishing Co., Easton, Pa., 15th Edition (1975), describes compositions and formulations suitable for pharmaceutical delivery of inactivated pathogens.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example, sodium acetate or sorbitan monolaurate.

For example, the pharmaceutical compositions (medicaments) can include one or more of a stabilizing detergent, a micelle-forming agent, and an oil. Suitable stabilizing detergents, micelle-forming agents, and oils are detailed in U.S. Pat. No. 5,585,103; U.S. Pat. No. 5,709,860; U.S. Pat. No. 5,270,202; and U.S. Pat. No. 5,695,770. A stabilizing detergent is any detergent that allows the components of the emulsion to remain as a stable emulsion. Such detergents include polysorbate, 80 (TWEEN) (Sorbitan-mono-9-octadecenoate-poly(oxy-1,2-ethanediyl; manufactured by ICI Americas, Wilmington, Del.), TWEEN 40™, TWEEN 20™, TWEEN 60™, Zwittergent™ 3-12, TEEPOL HB7™, and SPAN 85™. These detergents are usually provided in an amount of approximately 0.05 to 0.5%, such as at about 0.2%. A micelle forming agent is an agent which is able to stabilize the emulsion formed with the other components such that a micelle-like structure is formed. Such agents generally cause some irritation at the site of injection in order to recruit macrophages to enhance the cellular response. Examples of such agents include polymer surfactants described by, e.g., Schmolka, J. Am. Oil. Chem. Soc. 54:110, 1977, and Hunter et al., J. Immunol. 127:1244, 1981, and such agents as PLURONIC™ L62LF, L101, and L64, PEG1000, and TETRONIC™ 1501, 150R1, 701, 901, 1301, and 130R1. The chemical structures of such agents are well known in the art. In one embodiment, the agent is chosen to have a hydrophile-lipophile balance (HLB) of between 0 and 2, as defined by Hunter and Bennett, J. Immun. 133:3167, 1984. The agent can be provided in an effective amount, for example between 0.5 and 10%, or in an amount between 1.25 and 5%.

The oil included in the composition is chosen to promote the retention of the pathogen in oil-in-water emulsion, and preferably has a melting temperature of less than 65° C., such that emulsion is formed either at room temperature, or once the temperature of the emulsion is adjusted to room temperature. Examples of such oils include squalene, Squalane, EICOSANE™, tetratetracontane, glycerol, and peanut oil or other vegetable oils. In one specific, non-limiting example, the oil is provided in an amount between 1 and 10%, or between 2.5 and 5%. The oil should be both biodegradable and biocompatible so that the body can break down the oil over time, and so that no adverse affects, such as granulomas, are evident upon use of the oil.

Optionally, the pharmaceutical compositions or medicaments can include a suitable adjuvant to increase the immune response against the pathogen. As used herein, an "adjuvant" is any potentiator or enhancer of an immune response. The term "suitable" is meant to include any substance which can be used in combination with the selected pathogen to augment the immune response, without producing adverse reactions in the vaccinated subject. Effective amounts of a specific adjuvant may be readily determined so as to optimize the potentiation effect of the adjuvant on the immune response of a vaccinated subject. For example, suitable adjuvants in the context of vaccine formulations include 0.5%-5% (e.g., 2%) aluminum hydroxide (or aluminum phosphate) and MF-59 oil emulsion (0.5% polysorbate 80 and 0.5% sorbitan trioleate. Squalene (5.0%) aqueous emulsion) is another adjuvant which has been favorably utilized in the context of vaccines. For example, the adjuvant can be a mixture of stabilizing detergents, micelle-forming agent, and oil available under the name Provax® (IDEC Pharmaceuticals, San Diego, Calif.). An adjuvant can also be an immunostimulatory nucleic acid, such as a nucleic acid including a CpG motif. Other adjuvants include mineral, vegetable or fish oil with water emulsions, incomplete Freund's adjuvant, *E. coli* J5, dextran sulfate, iron sulfate, iron oxide, sodium alginate, Bacto-Adjuvant, certain synthetic polymers such as Carbopol (BF Goodrich Company, Cleveland, Ohio), poly-amino acids and co-polymers of amino acids, saponin, carrageenan, REGRESSIN (Vetrepharm, Athens, Ga.), AVRIDINE (N,N-dioctadecyl-N',N'-bis(2-hydroxyethyl)-propanediamine), long chain polydispersed .beta. (1,4) linked mannan polymers interspersed with O-acetylated groups (e.g., ACEMANNAN), deproteinized highly purified cell wall extracts derived from non-pathogenic strain of *Mycobacterium* species (e.g., EQUIMUNE, Vetrepharm Research Inc., Athens Ga.), Mannite monooleate, paraffin oil and muramyl dipeptide. A suitable adjuvant can be selected by one of ordinary skill in the art.

The pharmaceutical compositions (medicaments) can be prepared for use in therapeutic or prophylactic regimens (e.g., vaccines) and administered to human or non-human subjects to elicit an immune response against one or more pathogens. For example, the compositions described herein can be administered to a human (or non-human) subject to elicit a protective immune response against one or more pathogens. To elicit an immune response, a therapeutically effective (e.g., immunologically effective) amount of the inactivated pathogen is administered to a subject, such as a human (or non-human) subject.

A "therapeutically effective amount" is a quantity of a composition used to achieve a desired effect in a subject being treated. For instance, this can be the amount necessary to stimulate an immune response, to prevent infection, to reduce symptoms, or inhibit transmission of a pathogen. When administered to a subject, a dosage will generally be used that will achieve target tissue concentrations (for example, in antigen presenting cells) that is empirically determined to achieve an in vitro effect. Such dosages can be determined without undue experimentation by those of ordinary skill in the art.

An immunogenic composition, such as a vaccine composition containing an inactivated pathogen, can be administered by any means known to one of skill in the art, such as by intramuscular, subcutaneous, or intravenous injection, but even oral, nasal, and transdermal routes are contemplated. In one embodiment, administration is by subcutaneous or intramuscular injection. To extend the time during which the inactivated pathogen is available to stimulate a response, the peptide can be provided as an oily injection, as a particulate system, or as an implant. The particulate system can be a microparticle, a microcapsule, a microsphere, a nanocapsule, or similar particle. A particulate carrier based on a synthetic polymer has been shown to act as an adjuvant to enhance the immune response, in addition to providing a controlled release.

As an alternative to liquid formulations, the composition can be administered in solid form, e.g., as a powder, pellet or tablet. For example, the vaccine composition can be administered as a powder using a transdermal needleless injection device, such as the helium-powered POWDERJECT® injection device. This apparatus uses pressurized helium gas to propel a powder formulation of a vaccine composition, e.g., containing an inactivated pathogen, at high speed so that the vaccine particles perforated the stratum corneum and land in the epidermis.

Polymers can be also used for controlled release. Various degradable and nondegradable polymeric matrices for use in controlled drug delivery are known in the art (Langer, Accounts Chem. Res. 26:537, 1993). For example, the block copolymer, polaxamer 407 exists as a viscous yet mobile liquid at low temperatures but forms a semisolid gel at body temperature. It has shown to be an effective vehicle for formulation and sustained delivery of recombinant interleukin-2 and unease (Johnston et al., Pharm. Res. 9:425, 1992; and Fults & Johnston, J. Parent. Sci. Tech. 44(2):58, 1990). Alternatively, hydroxyapatite has been used as a microcarrier for controlled release of proteins (Ijntema et al., Int. J. Pharm. 112:215, 1994). In yet another aspect, liposomes are used for controlled release as well as drug targeting of the lipid-capsulated drug (Betageri et al., Liposome Drug Delivery Systems, Technomic Publishing Co., Inc., Lancaster, Pa., 1993). Numerous additional systems for controlled delivery of therapeutic proteins are known (e.g., U.S. Pat. No. 5,055,303; U.S. Pat. No. 5,188,837; U.S. Pat. No. 4,235,871; U.S. Pat. No. 4,501,728; U.S. Pat. No. 4,837,028; U.S. Pat. No. 4,957,735; and U.S. Pat. No. 5,019,369; U.S. Pat. No. 5,055,303; U.S. Pat. No. 5,514,670; U.S. Pat. No. 5,413,797; U.S. Pat. No. 5,268,164; U.S. Pat. No. 5,004,697; U.S. Pat. No. 4,902,505; U.S. Pat. No. 5,506,206; U.S. Pat. No. 5,271,961; U.S. Pat. No. 5,254,342; and U.S. Pat. No. 5,534,496).

In one specific, non-limiting example, the inactivated pathogen (e.g., a parasite, such as a protozoan parasite) is administered to elicit a cellular immune response (e.g., a cytotoxic T lymphocyte (CTL) response). A number of means for inducing cellular responses, both in vitro and in vivo, are known. Lipids have been identified as agents capable of assisting in priming CTL in vivo against various antigens. For example, as described in U.S. Pat. No. 5,662,907, palmitic acid residues can be attached to the alpha and epsilon amino groups of a lysine residue and then linked (e.g., via one or more linking residues, such as glycine, glycine-glycine, serine, serine-serine, or the like) to an immunogenic peptide or protein. The lipidated peptide can then be injected directly in a micellar form, incorporated in a liposome, or emulsified in an adjuvant. As another example, E. coli lipoproteins, such as tripalmitoyl-S-glycerylcysteinlyseryl-serine can be used to prime tumor specific CTL when covalently attached to an appropriate peptide (see, Deres et al., Nature 342:561, 1989). Further, as the induction of neutralizing antibodies can also be primed with the same molecule conjugated to a peptide which displays an appropriate epitope, two compositions can be combined to elicit both humoral and cell-mediated responses where that is deemed desirable.

Dosages of inactivated pathogen are administered that are sufficient to elicit an immune response, e.g., a protective immune response, in a subject. With respect to viral pathogens, the dosage is typically calculated based on the amount of biological matter equivalent to a specified titer of infectious (e.g., virulent or attenuated) virus. For example, a dose equivalent to about $10^6$, or about $10^7$, or about $10^8$, or about $10^9$, or about $10^{10}$, or about $10^{11}$ or about $10^{12}$, or even more live virus per dose can be administered to elicit an immune response in a subject. In some cases, the dose includes an amount in excess of the amount of a live virus utilized to elicit an immune response, because the inactivated vaccine is incapable of increasing in number after administration into the subject. When calculating the amount of a cellular pathogen, e.g., a bacteria, a fungus or a parasite, the amount can be calculated by comparison to a dose of live bacteria, e.g., from about $10^3$ cells or organisms to about $10^{10}$ live organisms, depending on the formulation. For example, the dose can include at least about 100 nanograms (or 200 nanograms, or 500 nanograms, or 1 microgram) of protein antigen per dose to about 25 mg (e.g., about 10 mg, or about 15 mg, or about 20 mg), or even more of an inactivated pathogen. Typically the vaccine composition includes additional pharmaceutically acceptable constituents or components. Accordingly, the vaccine composition can include at least about 0.1% wt/wt inactivated pathogen to about 99% wt/wt inactivated pathogen, with the balance of the vaccine composition is made up of pharmaceutically acceptable constituents, such as a one or more pharmaceutically acceptable carrier, pharmaceutically acceptable stabilizer and/or pharmaceutically acceptable diluent. Guidelines regarding vaccine formulation can be found, e.g., in U.S. Pat. Nos. 6,890,542, and 6,651,655. Doses can be calculated based on protein concentration (or infectious units, such as PFU, of infectious unit equivalents). The optimal dosage can be determined empirically, for example, in preclinical studies in mice and non-human primates, followed by testing in humans in a Phase I clinical trial. Actual methods for preparing administrable compositions will be known or apparent to those skilled in the art and are described in more detail in such publications as Remington's Pharmaceutical Sciences, 19th Ed., Mack Publishing Company, Easton, Pa., 1995.

Typically, but not always, the vaccine compositions are administered prior to exposure of a subject to a pathogen, e.g., as a vaccine. Vaccine compositions can be prepared by inactivating a wide range of pathogens using hydrogen peroxide according to the methods described herein. For example, vaccine compositions can be prepared by inactivating a pathogenic virus with a solution containing hydrogen peroxide. Non-limiting examples of viruses that can be inactivated using hydrogen peroxide include: picornaviruses (including enteroviruses), paramyxoviruses, bunyaviruses, coronaviruses, adenoviruses, parvoviruses, retroviruses, togaviruses, arenaviruses, flaviviruses, herpesviruses, picornaviruses, hepadnaviruses, orthomyxoviruses, rhabdoviruses, and orthopoxviruses (e.g., poxviruses), such as poliovirus, measles virus, mumps virus, parainfluenza virus, Newcastle disease virus, rubella virus, Eastern and Western Equine Encephalitis Viruses, Lassa virus, lymphocytic choriomeningitis virus, West Nile virus, Dengue virus, Yellow fever virus, Tick-borne encephalitis virus, St. Louis encephalitis virus, Japanese Encephalitis virus, varicella zoster virus (VZV), cytomegalovirus, herpes simplex viruses, retroviruses including HIV (human immunodeficiency virus), hepatitis A virus, hepatitis B virus, hepatitis C virus, influenza viruses, rabies virus, molluscum contagiosum (a mulliscipoxvirus) and smallpox virus (typically, vaccinia virus).

Bacterial pathogens can also be inactivated using hydrogen peroxide for use in vaccine compositions. Non-limiting examples of bacteria that can be inactivated with hydrogen peroxide according to the methods described herein include: *Corynebacterium diptheriae, Bordatella pertussis, Clostridium tetani, Haemophilus influenzae, Streptococcus pneumoniae, Neisseria meningitides*, and *Bacillum anthracis*.

Vaccine compositions can also be produced from fungal pathogens inactivated using hydrogen peroxide. Exemplary fungal pathogens include: *Candida albicans, Aspergillus fumigatus*, and *Cryptococcus neoformans*. The methods disclosed herein can also be used to inactivate parasites, especially protozoan parasites, such as *Plasmodium falciparum* and other *Plasmodium* species, *Leishmania* (sp.), *Cryptosporidium parvum, Entamoeba histolytica*, and *Giardia lamblia*, as well as *Toxoplasma, Eimeria, Theileria*, and *Babesia* species.

It will be apparent that the precise details of the methods or compositions described can be varied or modified without departing from the spirit of the described invention. The following examples are provided to illustrate certain particular features and/or embodiments. These examples should not be construed to limit the invention to the particular features or embodiments described. Each of the references cited below is incorporated by reference for all purposes.

EXAMPLES

Example 1

Predominant Antigenic Epitopes are Retained Following Inactivation with Hydrogen Peroxide To demonstrate that predominant antigenic epitopes of pathogens were maintained following inactivation with hydrogen peroxide, an enzyme-linked immunosorbent assay (ELISA) was performed to evaluate whether known pathogen-specific antibodies could bind to hydrogen peroxide inactivated pathogen. Vaccinia-specific ELISA assays were performed as described by Hammarlund et al., (*Nature Medicine* 9:1131-1137, 2003), using untreated vaccinia (strain: WR) whole virus lysate or whole virus lysate inactivated using one of several different procedures: 1) heat inactivation at 56° C. for 2 hours; 2) heat inactivation at 100° C. for 10 minutes; 3) UV light 5 joules; 4) UV light 10 joules; 5) 1% formaldehyde for 2 hours; or 6) 3% hydrogen peroxide for 2 hours. Virus lysates were used at a 1:800 dilution in phosphate buffered saline (PBS). An internal positive control was included on each plate to normalize ELISA values between plates and between assays performed on different days. Approximately 1 year post-smallpox vaccination human plasma was used as a positive control sample (~normalized to 10,000 EU). Naïve human plasma from an unvaccinated subject was used as a negative control. A series of 3-fold dilutions (beginning at a 1:30 dilution) of plasma or serum was added to preblocked plates and incubated for 1 hour. After washing, plates were incubated for 1 hour with horseradish peroxidase-conjugated monoclonal mouse antibody to human IgG(γ) (PharMingen). After an additional washing step, detection reagents were added, followed by 1M HCL, and the plates were read on an ELISA plate reader. Antibody titers were determined by log-log transformation of the linear portion of the curve, with 0.1 optical density (O.D.) units used as the endpoint and conversion performed on final values.

Results of an exemplary ELISA are shown in FIG. 1. Heat inactivation or UV inactivation resulted in loss of virus-specific antibody binding to the viral antigen on the ELISA plate (that is, loss of ELISA titer), apparently due to destruction of antibody-binding epitopes. In contrast, viral antigen that was inactivated by hydrogen peroxide or formaldehyde retained their antigenic composition almost as well as the live virus that was not modified by any inactivation treatments.

Example 2

Immunogenicity of Vaccinia Virus Inactivated with Hydrogen Peroxide

Figure 2:
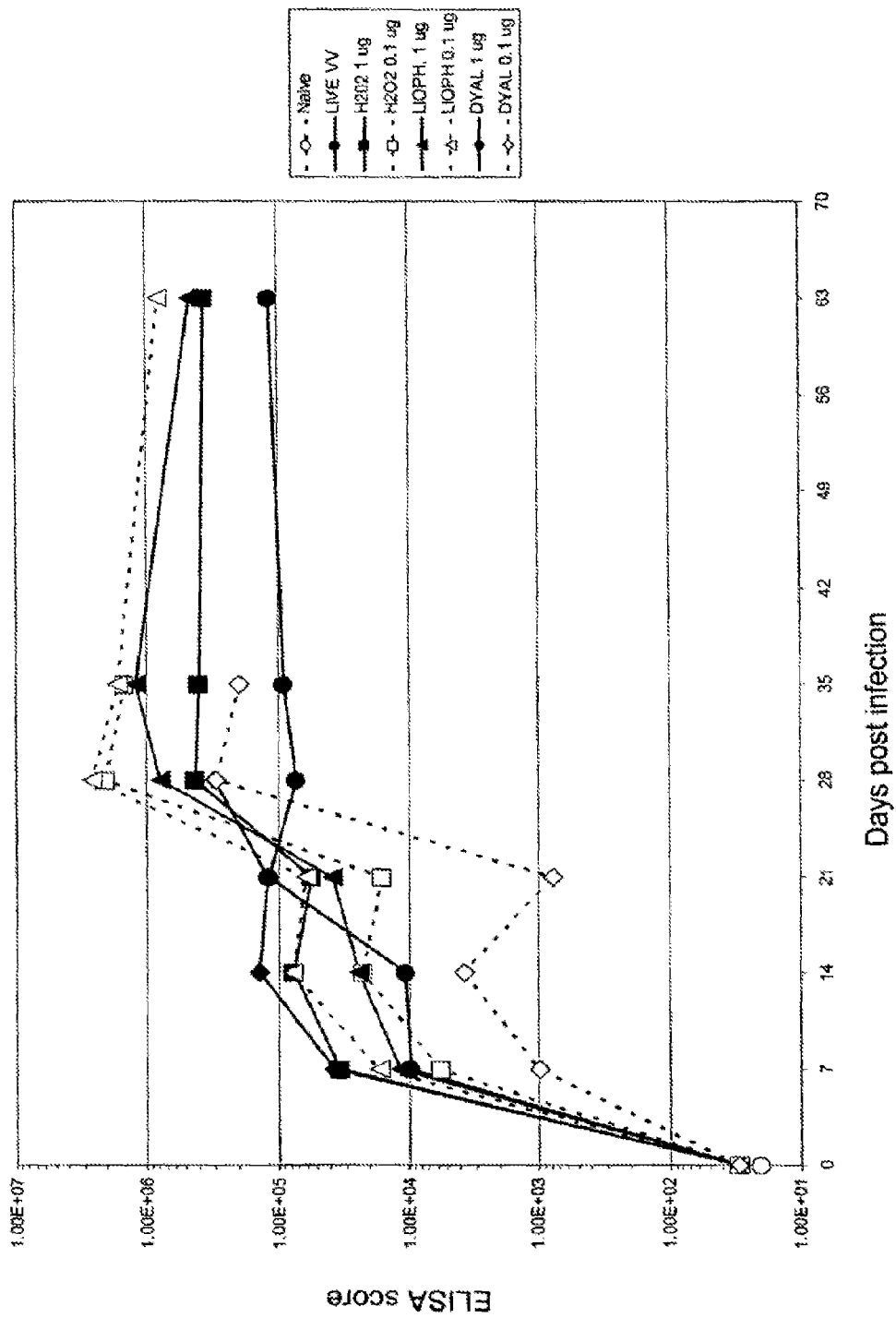
FIG. 2 is a line graph illustrating the results of an ELISA measuring vaccinia virus specific antibodies following administration of vaccinia virus vaccines prepared using different inactivation methods (● Live vaccinia virus (VV); ○ Naïve serum; ■ 1 μg $H_2O_2$ inactivated VV; □ 0.1 μg $H_2O_2$ inactivated VV; ▲ 1 μg $H_2O_2$ inactivated lyophilized VV; Δ 0.1 μg $H_2O_2$ inactivated lyophilized VV; ◆ 1 μg $H_2O_2$ inactivated dyalized VV; ◇ 0.1 μg $H_2O_2$ inactivated dyalized VV). ELISA score is shown on the Y axis and days post infection are indicated on the X axis.

To demonstrate that immunogenicity of hydrogen peroxide inactivated vaccinia virus is retained, mice were immunized with live vaccinia virus ($1 \times 10^7$ pfu) or two different concentrations of vaccinia virus inactivated with 3% hydrogen peroxide. A 1:10 volume of 30% hydrogen peroxide was added to a suspension of virus, resulting in a final concentration of 3% hydrogen peroxide during the inactivation procedure. The subject mice were injected with 1 μg (~$10^7$ pfu-equivalents of live virus) or 0.1 μg (~$10^6$ pfu-equivalents of live virus) in the hydrogen peroxide inactivating solution, or following dialysis against sterile PBS, or lyophilization and reconstitution in sterile water. Lyophilization was carried out at room temperature in a SPEED-VAC® concentrator (Savant). Live virus was injected intraperitoneally in a 500 μL volume of tissue culture medium. The inactivated vaccine preparations were mixed with a human FDA-approved adjuvant, MPL (monophosphoryl lipid A, sold by Corixa) immediately prior to intraperitoneal injection. Following booster vaccination (using the same vaccine preparation and the same dose of viral antigen) on day 21 after primary vaccination, a further increase in antibody titers was achieved. Mice that received live vaccinia infection were not boosted because in this case, the virus is a replicating antigen that is produced internally for several days acting as a "booster" following the primary injection. The hydrogen peroxide-inactivated virus vaccine was found to provide effective vaccination regardless of whether residual hydrogen peroxide was retained in the vaccine preparation during injection ($H_2O_2$ samples) or was removed by lyophilization and reconstitution (Lioph) or by dialysis (Dyal). As shown in FIG. 2, hydrogen peroxide inactivated virus retained immunogenicity, and elicited an immune response equivalent in titer to live vaccinia virus, regardless of post inactivation treatment.

Example 3

Inactivation of Pathogens by Very Low Concentrations of $H_2O_2$

To demonstrate that hydrogen peroxide effectively inactivates pathogens at across a wide range of concentrations, vaccinia virus was incubated with varying concentrations of hydrogen peroxide and infectivity was evaluated.

Virus was recovered following infection of BSC-40 cells at a MOI of 0.1 for 48 hours. Virus was harvested after cells show 100% CPE (cytopathic effect, usually 48 hrs post-infection) by scraping the cells off of the surface of the culture vessel. The cells and accompanying culture medium was centrifuged at 2000 rpm for 10 minutes at 4° C. (in a 50 ml conical tube). Cells were resuspended in 4 ml of 10 mM Tris-Cl ph 8, and the cell suspension was placed on ice for 15 minutes to cause the cells to swell. The suspension was mixed by Vortex every 3 minutes. The suspension was lysed using a Dounce homogenizer with a "tight" pestle for 50 strokes. The homogenate was centrifuged at 2000 rpm×10 minutes at 4° C. to spin out nuclei. The supernatant was removed using a pipet, and filtered using an 0.8 μM filter. The filtered supernatant was layered onto a 6 ml 36% sucrose cushion and placed on ice, while the pellet was resuspended in 2 ml of 10 mM Tris-Cl ph 8 and again homogenize as indicated above. This second homogenate was also centrifuged at 2000 rpm×10 minutes at 4° C. and the supernatant was removed and filtered with a 0.8 μM filter. The filtered supernatant was then layered onto the 36% sucrose cushion so that a total of (approximately) 6 ml of crude virus stock was layered over a 6 ml sucrose cushion. The filtered supernatant was separated by ultracentrifugation at 18000 rpm (55000 g)×80 minutes at 4° C. Membranous debris remained at the sucrose interface. Virus was pelleted. The supernatant was aspirated, and the virus pellet was resuspended in 500 μl of 10 mM Tris-Cl ph 8. The purified virus was evaluated by protein quantitation and plaque assay to determine yield and viability. The stock was stored at −80° C. until use.

Figure 3:
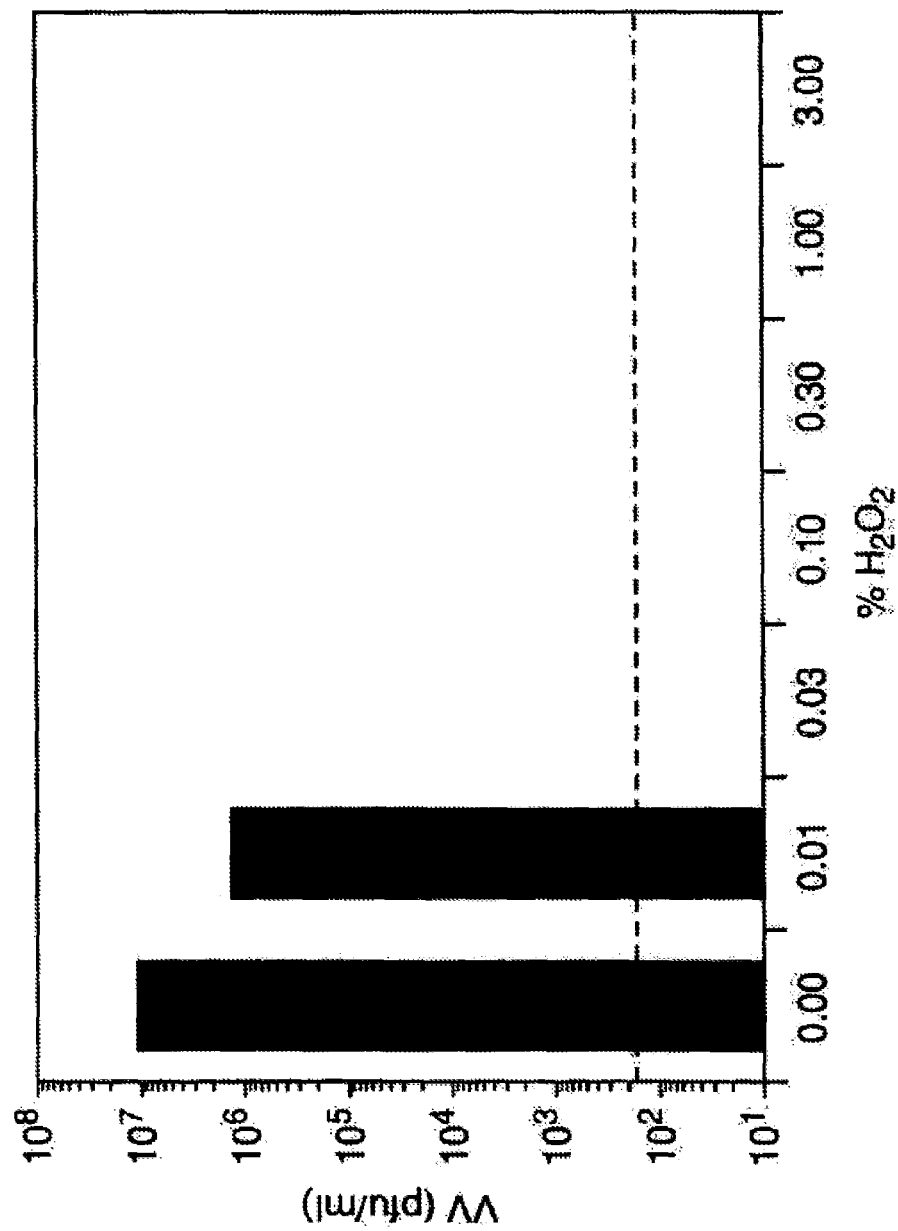
FIG. 3 is a bar graph illustrating inactivation of an exemplary pathogen at a wide range of $H_2O_2$ concentrations. Live virus titer is indicated on the Y axis (pfu/ml) and % $H_2O_2$ is indicated on the X axis.

Live vaccinia virus was exposed to different concentrations of $H_2O_2$ for 2 hours and then immediately diluted and tested for infectious virus by plaque assay. FIG. 3 graphically illustrates the results of an exemplary plaque assay.

Each plaque represents one infectious unit of virus and after treatment with $H_2O_2$ at concentrations as low at 0.03%, no infectious virus could be detected. These results demonstrated that $H_2O_2$ effectively inactivates pathogens, such as viruses, at concentrations as low as 0.03%.

Example 4

$H_2O_2$ Inactivated Vaccines Generate Desired Immune Responses

The ability of $H_2O_2$ inactivated pathogens to elicit a desired, (e.g., immunologically relevant) immune response was confirmed by vaccinating mice with inactivated vaccinia virus and measuring CD4+ and CD8+ T cell responses, and by plaque neutralization assay.

BALB/c mice were vaccinated intraperitoneally at 7 weeks of age with either $1 \times 10^7$ pfu live, replicating vaccinia virus (VV) or 5 µg of $H_2O_2$-inactivated VV mixed with MPL adjuvant according to manufacturer's directions. All animals receiving inactivated virus were boosted 21 days later using identical inoculations. Animals were euthanized at 41 days after the second vaccination (or 62 days after live infection). Splenocytes ($1 \times 10^6$/well) were stimulated with VV-infected A20 cells (MOI=5, 14 hr infection, $0.5 \times 10^6$/well) for 6 hours in the presence of Brefeldin A to block cytokine secretion and optimize intracellular cytokine staining (ICCS). Virus-specific IFNγ+TNFα+ T cells were measured by ICCS.

Figure 4A:
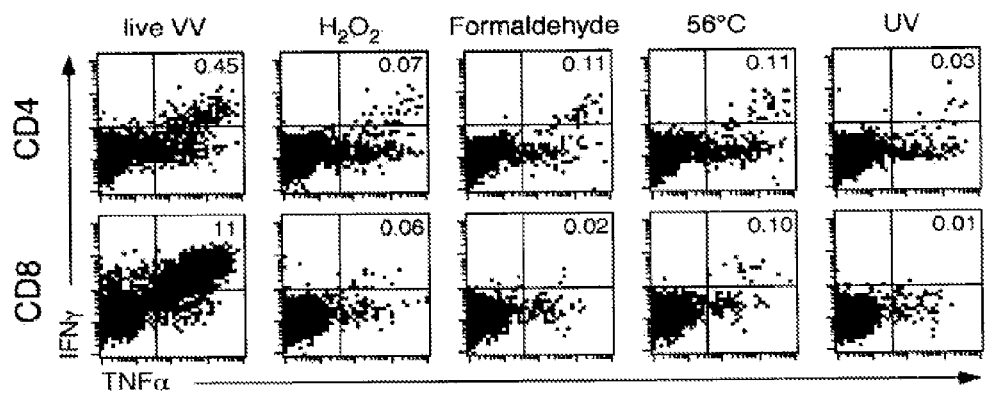
FIG. 4A is a series of dot plots depicting flow cytometric analysis of antigen specific CD4+ and CD8+ T cell subsets after administration of vaccinia virus vaccines prepared with different inactivation methods (from left to right: live virus; $H_2O_2$ inactivated virus; formaldehyde inactivated virus; heat inactivated virus; and UV inactivated virus).

FIG. 4A illustrates the induction of antiviral CD4+ and CD8+ T cell responses following immunization with $H_2O_2$-inactivated vaccinia virus (VV). In FIG. 4A, T cells were first gated on CD4 (top panels) or CD8 (bottom panels) and the numbers in the upper right quadrant indicate the percentage of virus-specific T cells determined after background subtraction from wells incubated in medium alone. This data is representative of 2-4 mice analyzed in 2 different experiments.

Figure 4B:
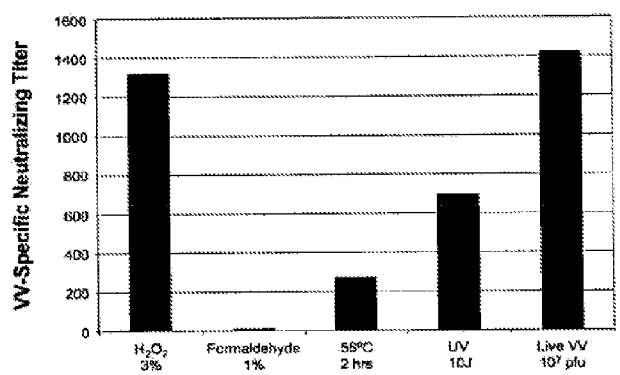
FIG. 4B is a bar graph illustrating measurement of neutralizing antibody titers specific for vaccinia virus (Y axis) following administration of vaccines prepared by different methods (from left to right: $H_2O_2$ inactivated; formaldehyde inactivated; heat inactivated; UV inactivated and live virus).
Figure 4C:
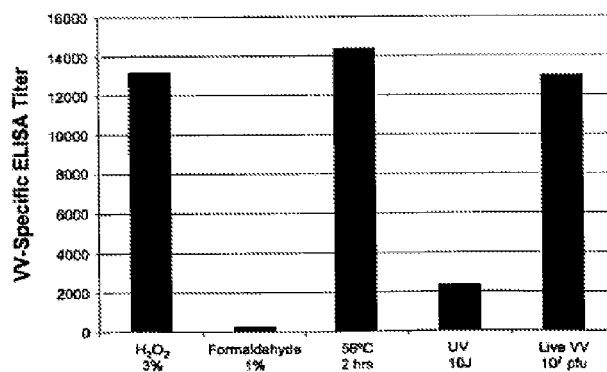
FIG. 4C is a bar graph illustrating the results of an ELISA detecting vaccinia virus specific antibodies (Y axis) following administration of vaccinia virus vaccines prepared by different methods (from left to right: $H_2O_2$ inactivated; formaldehyde inactivated; heat inactivated; UV inactivated and live virus).

To confirm that the antibody response following immunization with $H_2O_2$— inactivated vaccinia virus (VV) was a biologically relevant antiviral antibody response, BALB/c mice were vaccinated intraperitoneally at 7 weeks of age with either $1 \times 10^7$ pfu live, replicating vaccinia virus (VV) or 5 µg of VV inactivated with either 3% $H_2O_2$, 1% formaldehyde, Heat inactivation (56° C., 2 hours), or ultraviolet light (UV light, 10 joules) and administered with MPL adjuvant according to manufacturer's directions. All animals receiving inactivated virus were boosted 21 days later using identical inoculations. At 41 days after the second vaccination (or 62 days after live infection), antiviral antibody responses to vaccinia antigens were determined as shown in FIGS. 4B and C. Biologically relevant neutralizing antibodies (that is, antibodies capable of reducing virus infectivity) were determined and the dilution of serum antibody capable of reducing infectious virus by 50% ($NT_{50}$) is shown (FIG. 4B). Formaldehyde-inactivation produced poor antibody responses compared to other inactivation techniques. UV inactivation worked reasonably well, but was not as effective as $H_2O_2$. Heat inactivation resulted in strong antibody responses as measured by ELISA (FIG. 4C), but with poor neutralizing activity, indicating that most of the antibody response was mounted against non-protective epitopes. $H_2O_2$-inactivated vaccine was the only vaccine that demonstrated effective, biologically relevant antibody responses that closely mimicked the immunity induced by systemic live viral infection.

Example 5

$H_2O_2$ Effectively Inactivates a Wide Variety of Pathogens

Figures 5A, 5B:
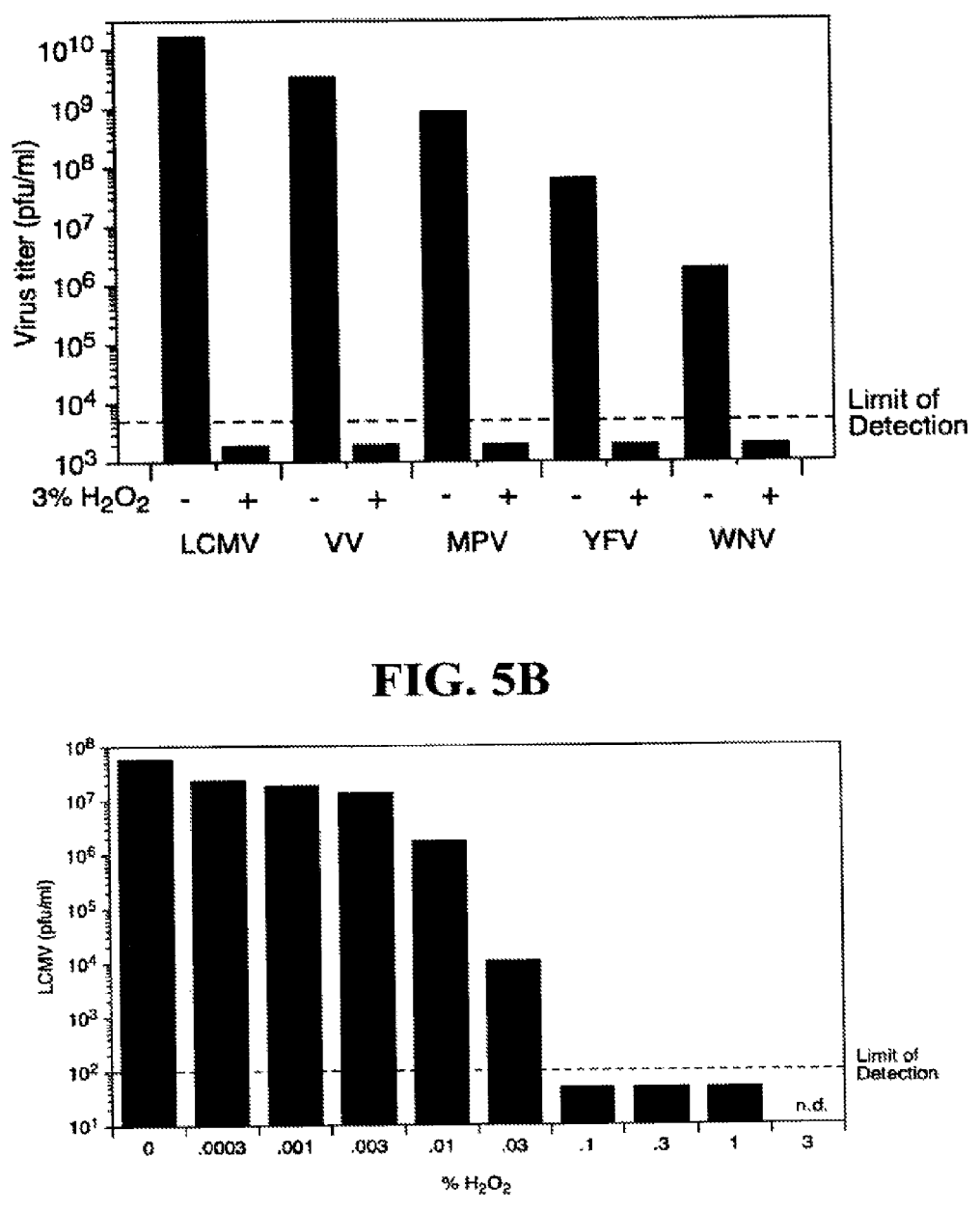

To confirm that $H_2O_2$ inactivates a broad range of pathogens, viability of several viruses belonging to different classes was measured following inactivation with $H_2O_2$. Viruses from different classes, including both DNA and RNA viruses, were inactivated in 3% $H_2O_2$ as described above. Viability was determined by measuring viral titer in appropriate host cells by plaque assay. As shown in FIG. 5A, lymphocytic choriomeningitis virus (LCMV), yellow fever virus (YFV), West Nile virus (WNV), vaccinia virus (VV) and monkeypox virus (MPV) were all effectively inactivated by treatment with $H_2O_2$, with viral titers in each case being reduced to below the limit of detection. As discussed above with respect to vaccinia virus, the capacity of $H_2O_2$ to inactivate virus is present at very low concentration regardless of the class of virus, as illustrated in FIG. 5B, which shows that infectivity of LCMV is eliminated at a concentration of less that 0.1% $H_2O_2$.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A method for producing an immunogenic composition comprising an inactivated viral pathogen, the method comprising: contacting a viral pathogen with a solution comprising a chemical oxidizing agent in an amount and for a time-period sufficient for the chemical oxidizing agent to render the viral pathogen noninfectious while retaining viral immunogenicity; and verifying immunogenicity of the noninfectious virus by using it to elicit a virus-specific antibody, B cell or T cell response, or to reduce infection by the pathogen, or decrease symptoms that result from infection by the pathogen, wherein producing an immunogenic vaccine composition comprising an inactivated viral pathogen is afforded.

2. The method of claim 1, wherein the oxidizing agent comprises hydrogen peroxide.

3. The method of claim 2, wherein the solution comprises at least about 0.03% hydrogen peroxide (wt/vol).

4. The method of claim 2, wherein the pathogen is contacted with the solution comprising hydrogen peroxide for at least about five minutes.

5. The method of claim 1, wherein the pathogen is contacted with the solution comprising the oxidizing agent at a temperature at or above 0° C.

6. The method of claim 1, comprising lyophilizing the solution to remove some, most or all of the oxidizing agent.

7. The method of claim 1, wherein the immunogenic composition is preservative-free.

8. The method of claim 1, wherein the inactivated pathogen is an immunogenically active pathogen.

9. The method of claim 1, wherein the pathogen is isolated or purified prior to contacting with the oxidizing agent.

10. The method of claim 6, wherein the steps of contacting the pathogen with the oxidizing agent and lyophilizing the solution are performed without an intervening purification step.

11. The method of claim 6, wherein the lyophilizing is performed according to good manufacturing (GMP).

12. The method of claim 1, wherein the virus is a pox virus, a flavivirus or an arenavirus.

13. The method of claim 12, wherein the virus is a vaccinia virus.

* * * * *